United States Patent [19]

Yamataka et al.

[11] 4,237,317
[45] Dec. 2, 1980

[54] PROCESS FOR PRODUCING SEBACIC ACID

[75] Inventors: Kazunori Yamataka; Yuuji Matsuoka; Toshiro Isoya, all of Nobeoka, Japan

[73] Assignee: Asahi Kasei Kogyo Kabushiki Kaisha, Tokyo, Japan

[21] Appl. No.: 923,703

[22] Filed: Jul. 11, 1978

[30] Foreign Application Priority Data

| Jul. 20, 1977 | [JP] | Japan | 52-86007 |
| Jul. 20, 1977 | [JP] | Japan | 52-86008 |
| Aug. 23, 1977 | [JP] | Japan | 52-100131 |
| Dec. 2, 1977 | [JP] | Japan | 52-144673 |
| May 24, 1978 | [JP] | Japan | 53-61122 |

[51] Int. Cl.$^2$ .................. C07C 51/00; C07C 55/20
[52] U.S. Cl. .................. 562/590; 204/59 R; 204/72; 204/79; 560/191; 560/204; 562/593
[58] Field of Search .......... 562/590; 204/59 R, 72–79; 560/191, 204

[56] References Cited

U.S. PATENT DOCUMENTS

| 2,858,335 | 10/1958 | Hill et al. | 562/593 |
| 3,896,011 | 7/1975 | Isaya et al. | 204/59 R |

FOREIGN PATENT DOCUMENTS

| 46-3816 | 11/1971 | Japan . |
| 46-37564 | 11/1971 | Japan . |
| 47-51327 | 12/1972 | Japan . |
| 49-75518 | 7/1974 | Japan . |
| 49-100024 | 9/1974 | Japan . |
| 49-101323 | 9/1974 | Japan . |

OTHER PUBLICATIONS

Chem. Abstracts, 69, 18555U (1968).
Kolbe, Ann. 69, 257 (1849).
J. Applied Chem. (USSR) 38, 1776–1781 (1956).

*Primary Examiner*—Vivian Garner
*Attorney, Agent, or Firm*—Armstrong, Nikaido, Marmelstein & Kubovcik

[57] ABSTRACT

Sebacic acid is produced from adipic acid by half esterifying adipic acid with methanol to produce monomethyl adipate, carrying out electrolytic condensation of the monomethyl adipate in a methanol solution containing an alkali metal salt of the monomethyl adipate to give an electrolytic solution containing dimethyl sebacate, treating the electrolytic solution by a combination of water treatment and anion exchange treatment or a combination of cation exchange treatment and anion exchange treatment to remove the monomethyl adipate and its alkali metal salt from the electrolytic solution, separating the dimethyl sebacate, and hydrolyzing the dimethyl sebacate to give sebacic acid.

36 Claims, 5 Drawing Figures

PROCESS FOR PRODUCING SEBACIC ACID

BACKGROUND OF THE INVENTION

This invention relates to a process for producing sebacic acid from adipic acid. More particularly, this invention relates to a process for producing sebacic acid by carrying out electrolytic condensation of monomethyl adipate.

Electrochemical condensation reactions of carboxylic acids are generally called as the Kolbe reaction and described in such references as H. Kolbe; *Ann.* 69, 257 (1849), A. C. Brown; *Ann.* 261, 107 (1891), etc. One example of the Kolbe reaction is the production of dimethyl sebacate from monomethyl adipate, in which the reaction at an anode can be represented by the following equation:

$$2CH_3OOC(CH_2)_4COO^- \xrightarrow{-2e} CH_3OOC(CH_2)_8COOCH_3 + 2CO_2$$

In order to produce sebacic acid from adipic acid industrially, it is necessary to pass through the following three steps, that is, (1) the first step comprises the production of monomethyl adipate, (2) the second step comprises the production of dimethyl sebacate from monomethyl adipate by electrolytic condensation and separation and purification of dimethyl sebacate from the electrolytic solution containing dimethyl sebacate, and (3) the third step comprises the production of sebacic acid. According to conventional processes, each step can be carried out, for example, as follows. Monomethyl adipate is produced by half esterifying adipic acid with methanol in the absence of a catalyst or in the presence of an acid catalyst (Japanese Patent Appln. Kokai (Laid-open) No. 100024/74). Electrolytic condensation of monomethyl adipate is carried out by dissolving monomethyl adipate in a methanol solution and electrolyzing the solution partly neutralized with an alkali such as potassium hydroxide to yield an electrolytic solution such as a methanol solution containing monomethyl adipate and its alkali metal salt, dimethyl sebacate, and trace amounts of by-products such as dimethyl adipate, methyl n-valerate, methyl ω-hydroxyvalerate, methyl allylacetate and the like, and subsequently separating dimethyl sebacate which is an electrolyzed product in the electrolytic solution from the starting monomethyl adipate and its alkali metal salt by extraction procedure (U.S. Pat. No. 3,896,011). Sebacic acid is obtained by hydrolyzing dimethyl sebacate thus separated and purified in the presence of an acid catalyst (U.S. Pat. No. 3,896,011).

In industrial scale production of sebacic acid according to a conventional process, there was the most important defect in the second step of separating dimethyl sebacate from the electrolytic solution containing dimethyl sebacate. That is, as a method for separating dimethyl sebacate from the electrolytic solution containing dimethyl sebacate, there are such methods as distillation, crystallization, extraction and the like. But as to a distillation method, since there is a defect in that dimethyl sebacate and monomethyl adipate produce an azeotropic mixture, it is not preferable to use the distillation method for the separation. Further in a crystallization method, since it is necessary to carry out the procedure at a low temperature, there is a defect in that contamination with monomethyl adipate and its alkali metal salt is inevitable during the crystallization of dimethyl sebacate. Therefore, there has been employed an extractive separation method by adding water, hexane, heptane and the like to the electrolytic solution. But according to said method, if water is used as an extracting agent, there are defects in that a large quantity of water should be used, and the separation of the oil layer and the water layer after the extraction is very difficult due to a very small difference of specific gravities of the two layers; and if an organic solvent such as n-heptane is used as an extracting agent, there is a defect in that it is inevitable to accompany more than a certain amount of monomethyl adipate to the n-heptane layer. According to the most recent method described in U.S. Pat. No. 3,896,011, the separation of highly pure dimethyl sebacate is successfully carried out by using a comparatively small amount of an extracting agent, i.e. by adding an organic solvent, which dissolves dimethyl sebacate but does not dissolve water, together with water to the electrolytic solution and separating after a prescribed contact time. But even in the most recent process as mentioned above, the defects of the conventional processes are not solved fundamentally. That is, the new insertion of water and an organic solvent into the system is inevitable, and the use of more than a certain amount of an extracting solvent is necessary in order to separate highly pure dimethyl sebacate: these are defects of said process.

The present inventors have studied earnestly to overcome the defects of the conventional processes and found that monomethyl adipate in the electrolytic solution can be separated by adsorption with anion exchange treatment, an alkali metal salt of monomethyl adipate can be separated by extraction with an extremely small amount of water or by adsorption with cation exchange treatment as alkali metal ions, and further monomethyl adipate adsorbed on the anion exchanger can easily be regenerated by methanol or water present in the system and alkali metal ions adsorbed on the cation exchanger can easily be regenerated by monomethyl adipate and/or a methanol solution containing monomethyl adipate present in the system. Consequently it has become possible to easily separate dimethyl sebacate from monomethyl adipate and its alkali metal salt and to afford highly pure dimethyl sebacate without introducing newly an organic solvent and water into the system or in some cases by only introducing an extremely small amount of water into the system.

SUMMARY OF THE INVENTION

It is an object of this invention to provide a process for producing sebacic acid from adipic acid overcoming the defects of conventional processes. It is another object of this invention to provide a process for producing sebacic acid from adipic acid industrially favorably by carrying out the separation of dimethyl sebacate remarkably easily in the second step. Further objects and advantages of this invention will be apparent to one skilled in the art from the accompanying disclosure and discussion.

This invention provides a process for producing sebacic acid from adipic acid which comprises half esterifying adipic acid with methanol to produce monomethyl adipate;

conducting electrolytic condensation of the monomethyl adipate in a methanol solution containing an alkali metal salt of monomethyl adipate to give an electrolytic solution containing dimethyl sebacate;

recovering dimethyl sebacate from the electrolytic solution by extracting the alkali metal salt of monomethyl adipate from the electrolytic solution with water after removal of the methanol and treating the electrolytic solution with an anion exchanger packed in a fixed bed to separate the monomethyl adipate therefrom, the water extraction and the anion exchange treatment being carried out successively or simultaneously;

or alternatively recovering dimethyl sebacate from the electrolytic solution by treating the electrolytic solution with a cation exchanger packed in a fixed bed to separate the alkali metal ions therefrom, treating the electrolytic solution with an anion exchanger packed in a fixed bed to separate the monomethyl adipate therefrom, the cation exchange treatment and the anion exchange treatment being carried out successively or simultaneously, and removing the methanol from the electrolytic solution at a desired time;

and hydrolyzing the resulting dimethyl sebacate to produce sebacic acid.

DETAILED DESCRIPTION OF THE INVENTION

Figure 1:
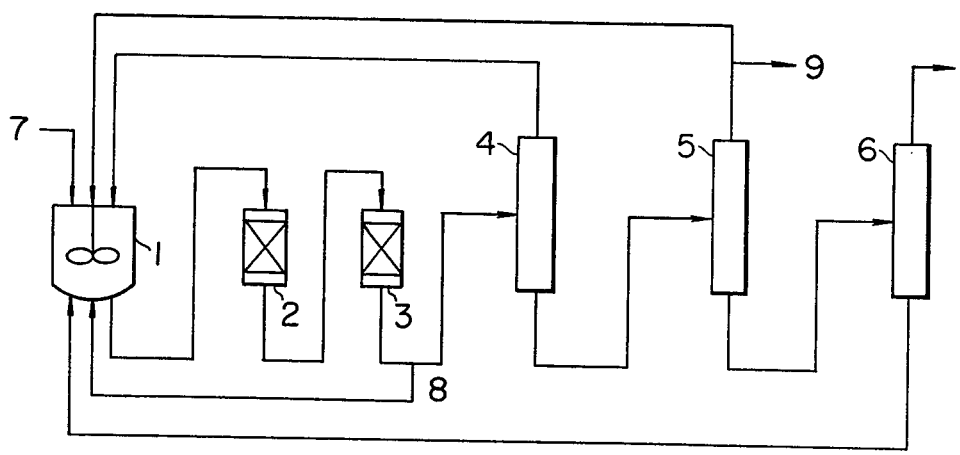
FIG. 1 is a schematic flow diagram suitable for practicing the first step of this invention.

The first step of this invention wherein monomethyl adipate is obtained by half esterification of adipic acid will be explained in detail below.

The composition of a starting material solution is generally sufficient if it contains adipic acid and methanol. In order to suppress the formation of dimethyl adipate and to produce monomethyl adipate favorably, it is preferable to use a starting material solution containing 1 mole of adipic acid, 0.2 to 2 moles of dimethyl adipate, 0.5 to 5 moles of methanol and 1 to 10 moles of water.

The reaction can be carried out by using an acid catalyst, for example, mineral acids such as sulfuric acid, hydrochloric acid, nitric acid, and the like and organic sulfonic acids such as p-toluenesulfonic acid and the like. In this case, the reaction conditions are not particularly limited but it is preferable to carry out the reaction under a pressure of 1 atmosphere or more and at a temperature of 50° C. or more. The reaction can also be carried out in the absence of a catalyst. In this case, the reaction can preferably be carried out at high temperatures and under pressure, for example, a pressure of 2 to 15 atmospheres and a temperature of 120° to 200° C. It is also possible to carry out the reaction by using a strongly acidic cation exchange resin as an acid catalyst. In this case, the use of strongly acidic cation exchange resin is disadvantageous in catalytic capacity but advantageous in corrosion of the reactor, etc. and separation of the reaction product from the catalyst, comparing with the case using a mineral acid or an organic sulfonic acid as a catalyst. Further, comparing with the case of using no catalyst, it may be disadvantageous in using a catalyst without fail but advantageous from the viewpoint of the reaction conditions and formation of by-products. In the case of carrying out the reaction without using a catalyst, it is necessary to conduct the reaction at high temperatures under pressure for a long time, and further by continuing the production of monomethyl adipate under such conditions for a long time industrially, the by-production of cyclopentanone increases as shown in the curve A in FIG. 2 and the by-production of high-boiling compounds also increases. Such by-productions are found to be caused by trace amounts of metal ions, particularly iron ions, which are released from the reactor itself into the reaction solution by the reaction under severe conditions such as high temperatures under pressure and which act as a catalyst to produce cyclopentanone as well as the high-boiling compounds. In industrial production of monomethyl adipate, it is usual to separate unreacted adipic acid during a purification procedure of monomethyl adipate and to recycle to the starting material solution. In such a case, it is also found that metal ions are released from a distillation still other than the reactor during the purification procedure of monomethyl adipate. Taking these facts into consideration, it is the most preferable process to use the strongly acidic cation exchange resin as a catalyst in industrial production of monomethyl adipate.

The strongly acidic cation exchange resin includes a polystyrene series resin such as styrene-divinylbenzene copolymers having sulfonic acid groups and having either gel type structure or porous type structure. In order to carry out the esterification reaction continuously and to show the activity of the cation exchange resin effectively, it is necessary to use the resin as a fixed bed. If the strongly acidic cation exchange resin is used continuously for a long period of time, catalytic activity of the resin in the esterification is gradually lowered due to an increase of metal ions adsorbed on the resin. In such a case, the cation exchange resin can be regenerated by a conventional regeneration method widely used such as regeneration with an aqueous nitric acid solution and can be used again.

As to a reaction temperature in the fixed bed packed with the strongly acidic cation exchange resin, higher temperatures are more effective from the viewpoint of reaction rate, but taking heat resistance of the resin into consideration, a temperature of 120° C. or less, particularly 90° C. or less, is preferable. But since too low reaction temperature takes a longer reaction time, a temperature of from 60° C. to 90° C. is practically preferable.

On the other hand, when the starting material solution is passed through the fixed bed packed with the strongly acidic cation exchange resin, deposition of adipic acid from the starting material solution at an operational temperature of the fixed bed is not preferable. Prevention of the deposition of adipic acid from the starting material solution may be possible if the amounts of the solvents such as methanol, water and dimethyl adipate are maintained larger than a certain amount. But the use of solvents in large excess is not preferable due to the necessary removal of the solvents during a procedure of separation and purification of monomethyl adipate from the reaction solution. Thus, in order to prevent the deposition of adipic acid from the starting material solution without using a large excess of solvent, it is necessary to supplement shortage of the solvents in the starting material solution by recycling a part of the effluent from the fixed bed. Recycling amount of the effluent from the fixed bed varies depending upon the amounts of adipic acid and the solvents in the starting material solution as well as the temperature of the fixed bed and cannot be limited, but it will be sufficient so as not to deposit adipic acid from the starting material solution. Further a flowing rate of the starting material solution passing through the fixed bed is not limited particularly, but it is preferable to set the flowing rate so that the esterification reaction in the fixed bed can proceed near the equilibrium.

One example of the process for producing monomethyl adipate by using a strongly acidic cation exchange resin as a catalyst will be explained hereinafter referring to the schematic flow diagram of FIG. 1. To a dissolving vessel 1, adipic acid and methanol are fed through an inlet 7 and methanol and water, dimethyl adipate and water, adipic acid and monomethyl adipate, and a part of the reaction solution, each taken off from the top of distillation column 4, from the top of distillation column 5, from the bottom of distillation column 6, and from a drain 8, respectively, are recycled to the dissolving vessel 1. In the dissolving vessel 1, adipic acid is dissolved and passes to the top of ion exchange resin column 2 as a starting material solution. In the ion exchange resin column 2, adsorption of trace amounts of metal ions and a part of the esterification reaction take place. From the bottom of ion exchange resin column 2, the liquid from which the metal ions have been removed is taken off and passes to the top of ion exchange resin column 3, wherein the esterification reaction mainly takes place. It is necessary to regenerate the resin in the ion exchange resin column 2 by a conventional regeneration method, for example, by using an aqueous nitric acid solution, if the liquid taken off out of the ion exchange resin column 2 becomes to contain more metal ions than the permissible concentration. Since the adsorption of metal ions and the esterification reaction are carried out separately by using two ion exchange resin columns, operational control of the ion exchange resin columns is very easy. From the bottom of the ion exchange resin column 3, there is taken off the esterification reaction solution, a part of which is recycled to the dissolving vessel 1 via the drain 8, and a part of which passes to the distillation column 4. On the other hand, concentrations of cyclopentanone and iron ion in the esterification reaction solution with the lapse of time can be controlled at very low level as shown in the curves C and D in FIG. 2. In the distillation column 4, methanol and water are distilled off and the residual liquid is taken out of the bottom of the column 4 and passes to the distillation column 5. The methanol and water distilled off from the top of the distillation column 4 are recycled to the dissolving vessel 1. In the distillation column 5, dimethyl adipate and water are distilled off and the residual liquid is taken out of the bottom of the column 5 and passes to the distillation column 6. The dimethyl adipate and water distilled off from the top of the distillation column 5 are separated into two layers and after removing a part of the water from a drain 9, the residue is recycled to the dissolving vessel 1. Monomethyl adipate is obtained from the top of the distillation column 6 and the residual liquid containing adipic acid and monomethyl adipate is taken out of the bottom of the column and recycled to the dissolving vessel 1.

The production of dimethyl sebacate by electrolytic condensation in the second step of this invention from monomethyl adipate obtained in the first step will be explained in detail below.

The electrolytic solution to be used in electrolytic condensation comprises monomethyl adipate and its neutralized salt, dimethyl sebacate and methanol.

As to a water concentration in the electrolytic solution, relationship between water concentration and current efficiency, water concentration and material yield is known (e.g. Journal of Applied Chemistry (U.S.S.R.) 38, 1776 (1956)). In order to maintain the current efficiency and the material yield high, it is necessary to lower the water concentration to 5% by volume or less. Further it has been believed that the maximum current efficiency and material yield can be obtained by decreasing the water concentration as low as possible. But the present inventors unexpectedly found that extreme decrease in water concentration rather lowers the current efficiency after a number of experiments. That is, as shown in Table 3 in Example 13, if water concentration in the electrolytic solution becomes less than 0.15% by weight, current efficiency decreases remarkably. On the other hand, if water concentration is more than 3.0% by weight, it was also found that the current efficiency and the material yield also decrease. Therefore, in order to maintain the current efficiency and the material yield at high level, it is necessary to maintain the water concentration in the electrolytic solution in the range of 0.15 to 3.0% by weight.

In order to increase electric conductivity of the electrolytic solution, there can be used as neutralization bases hydroxides, carbonates, bicarbonates, methylates, and ethylates of sodium, potassium or lithium or amines. But since an amine is oxidized at the anode to accelerate the consumption of the anode and the use of a lithium compound lowers the current efficiency, it is preferable to use hydroxides, carbonates, bicarbonates and methylates of sodium or potassium.

Neutralization degree of monomethyl adipate (defined as molar ratio for neutralizing monomethyl adipate with a base) is preferably 10 to 60% by mole, more preferably 20 to 50% by mole. If the neutralization degree is less than 10% by mole, the voltage is heightened, and if more than 60% by mole, the current efficiency is lowered.

Concentration of dimethyl sebacate in the electrolytic solution is preferably 5 to 40% by weight, more preferably 10 to 30% by weight. If the concentration is less than 5% by weight, the current efficiency is low, while if the concentration is more than 40% by weight, the voltage is heightened. Concentration of monomethyl adipate in the electrolytic solution is preferably 5-20% by weight.

As an electrolytic cell, there can be used any ones which are usually employed in organic electrolytic reactions and which can pass an electrolytic solution between the two electrodes with high flow rate. For example, there can be used an electrolytic cell comprising a cathode plate and an anode plate directed in parallel and a polyethylene plate placed between the two electrodes of determining the distance between the two electrodes. The polyethylene plate has an opening zone in its central part in order to pass the electrolytic solution. Electricity passing area of the electrodes is determined depending upon the area of the opening zone and the electrode distance depending upon the thickness of the polyethylene plate. The electrolytic solution is fed through a feed opening of the electrolytic cell, passed through between the two electrodes while bringing about the reaction, and recycled to an electrolytic solution tank after leaving an outlet.

As materials of the electrodes, platinum, rhodium, ruthenium, iridium, and the like alone or as an alloy can be used as an anode. These metals are generally used in the galvanized form by using titanium, tantalum, and the like as a substrate. As a cathode, those having low hydrogen overvoltage are preferable but not limited thereto particularly. Platinum, iron, stainless steel, titanium, and the like can be used as the cathode.

Flow rate of the electrolytic solution in the electrolytic cell is preferably 1 to 4 m/sec, more preferably 1 to 3 m/sec. If the flow rate is smaller than 1 m/sec, current efficiency becomes lower, while if greater than 4 m/sec, pressure loss in the electrolytic cell becomes greater.

The distance between the electrodes is preferably 0.5 to 3 mm, more preferably 0.5 to 2 mm. If the distance is less than 0.5 mm, pressure loss in the electrolytic cell becomes greater, while if more than 3 mm, the voltage becomes higher.

Current density is preferably 5 to 40 $A/dm^2$, more preferably 10 to 30 $A/dm^2$. If the current density is less than 5 $A/dm^2$, current efficiency becomes lower.

Temperature of the electrolytic solution is preferably 45° to 65° C., more preferably 50° to 60° C. If the temperature is lower than 45° C., current efficiency becomes lower and the voltage becomes higher.

Temperatures higher than 65° C. are limited by the boiling point of an electrolytic solution.

Separation and purification of dimethyl sebacate from the electrolytic solution containing dimethyl sebacate obtained by the above-mentioned electrolytic condensation in the second step of this invention will be explained in detail below.

In order to obtain dimethyl sebacate from a methanol solution of the electrolytic solution containing monomethyl adipate and its metal salt, dimethyl sebacate, and other trace amounts of by-products obtained by the electrolytic condensation, the following steps are necessary; that is, a step for removing the methanol by distillation, a step for separating alkali metal salt of monomethyl adipate or alkali metal ions, and a step for separating monomethyl adipate.

In the step for separating monomethyl adipate from the electrolytic solution, anion exchange treatment is carried out.

In the anion exchange treatment, the use of various anion exchangers may be possible, but in practice, the use of an anion exchange resin is preferable. As the anion exchange resin, there may be used strongly basic anion exchange resins having quaternary ammonium groups as exchanging groups, weakly or intermediately basic anion exchange resins having primary to tertiary amine groups as exchanging groups, and the like. If methanol or hot water is used as regenerant as will be explained below, weakly or intermediately basic anion exchange resins are advantageous industrially, particularly tertiary amine type anion exchange resins are preferable among them, taking regeneration efficiency and heat resistance of the resins into consideration. If methanol is used as regenerant, strongly basic anion exchange resins having pyridinium groups as exchanging groups can be used advantageously industrially in addition to weakly or intermediately basic anion exchange resins.

In the case of either using weakly basic, intermediately basic or pyridinium type anion exchange resins alone as an anion exchange resin, or using such an anion exchange resin together with a cation exchange resin as a mixed-bed as will be explained below, since the presence of methanol prevents adsorption of monomethyl adipate on the anion exchange resin, it is necessary to control the presence of methanol as low as possible. Generally, it is preferable to control the concentration of methanol in the feeding solution to the fixed bed packed with the ion exchange resin and in the remaining solution in the fixed bed 5% by weight or less. Therefore, in this case, it is necessary to remove the methanol from the electrolytic solution before the anion exchange treatment.

As a regenerant of the anion exchange resins, there may be used water or a hydrophilic organic solvent such as methanol, ethanol, acetone, tetrahydrofuran, etc. An industrially useful regenerant is methanol or heated water in the case of the treatment in combination with water treatment, and methanol in the case of the treatment in combination with cation exchange treatment. Particularly, the use of methanol is preferable, since the methanol removed from the electrolytic solution can advantageously be used. As to a regeneration temperature, higher temperatures are preferable from the viewpoint of regeneration efficiency, but lower temperatures are preferable from the viewpoint of boiling points of regenerants and heat resistance of the resins. In general, it is preferable to use methanol of from room temperature to 60° C. or hot water of 80° to 90° C. as a regenerant in the case of weakly or intermediately basic anion exchange resins. In the case of strongly basic anion exchange resins having quaternary ammonium groups as exchanging groups, it is preferable to use methanol of from room temperature to 40° C. as a regenerant.

In the next place, in the step for separating an alkali metal salt of monomethyl adipate or alkali metal ions, water treatment or cation exchange treatment is conducted.

The water treatment can be conducted before or after the anion exchange treatment or at the same time by using a fixed bed packed with anion exchanger as an extraction column. In either case, extraction effect of the alkali metal salt of monomethyl adipate by the water layer is not changed, but the anion exchange treatment after the water treatment is preferable from the viewpoint of adsorption of monomethyl adipate on the anion exchanger. Further, in order to separate a water addition solution into two layers during the water treatment, it is necessary to remove the methanol before the water treatment. Therefore, it is practically preferable to conduct the removal of methanol from the electrolytic solution, the water treatment, and the anion exchange treatment successively in this order. The amount of water used in the extraction treatment with water is sufficient if two layers can be separated after mixing the oil and water layers, but usually, it is preferable to use 5 to 50% by weight of water based on the weight of the electrolytic solution after removing the methanol.

The cation exchange treatment, wherein only alkali metal ions are separated by adsorption from an alkali metal salt of monomethyl adipate to liberate monomethyl adipate, is preferably conducted before the anion exchange treatment or should be conducted at least at the same time as the anion exchange treatment. Various cation exchanger may possibly be used for the cation exchange treatment, but in practice, it is preferable to use a cation exchange resin if the cation exchange treatment is conducted alone. If the cation exchange treatment is conducted at the same time as the anion exchange treatment, a mixed-bed of a cation exchange resin and an anion exchange resin can preferably be used or an amphoteric ion exchange resin having cation exchange groups and anion exchange groups can preferably be used. Since the presence of methanol hardly influences cation exchange treatment effect, the removal of the methanol from the electrolytic solution can be conducted at any time during the cation exchange treatment unlike the above-mentioned water treatment.

Cation exchange resins used in the cation exchange treatment are not particularly limited, but weakly or intermediately acidic cation exchange resins are advantageous industrially considering regeneration efficiency when monomethyl adipate and/or a methanol solution of monomethyl adipate are used as a regenerant. Among them, taking exchange capacity into consideration, acrylic acid type or iminodiacetic acid type cation exchange resins are preferable among weakly acidic cation exchange resins, and phosphonic acid type cation exchange resins are preferable among intermediately acidic cation exchange resins.

As a regenerant of the cation exchange resins, there may be used monomethyl adipate and/or an aqueous solution or hydrophilic organic solvent such as methanol, ethanol, acetone, tetrahydrofuran or the like containing monomethyl adipate. Among them, monomethyl adipate and/or a methanol solution containing monomethyl adipate are preferable industrially. If the cation exchange resin is used together with the anion exchange resin in a mixed-bed, since regeneration of the cation exchange resin and regeneration of the anion exchange resin should be conducted at the same time, it is necessary to use as a regenerant monomethyl adipate and methanol in this order. Even if methanol is used alone, since monomethyl adipate is desorbed by regeneration of the anion exchange resin to produce a methanol solution of monomethyl adipate, regeneration of the cation exchange resin also becomes possible. As the monomethyl adipate, the starting material fed to the electrolytic reaction can be used; as the methanol solution containing monomethyl adipate, an effluent from the regeneration of the anion exchange resin can be used; and as the methanol, that removed from the electrolytic solution can be used; so that it is not necessary to feed a new regenerant into the system. As to a regeneration temperature, higher temperatures are preferable from the viewpoint of regeneration efficiency, but a temperature range of from room temperature to 60° C. is usually used taking the boiling point of a regenerant and heat resistance of the resin into consideration.

The amphoteric ion exchange resin which is used in the case of conducting the cation exchange treatment and the anion exchange treatment at the same time is not particularly limited. But if methanol is used as a regenerant, the use of an amphoteric ion exchange resin comprising weakly or intermediately basic functional groups and weakly acidic functional groups is preferable from the viewpoint of regeneration efficiency. As the weakly or intermediately basic functional groups, primary to tertiary amines can be used, but the use of tertiary amines is preferable from the viewpoint of exchange capacity. As the weakly acidic functional groups, acrylic acid type and methacrylic acid type functional groups can be used, but the use of acrylic acid type functional groups is preferable from the viewpoint of exchange capacity. Therefore, an amphoteric ion exchange resin having tertiary amine and acrylic acid type functional groups is the most preferable industrially. The proportions of the weakly or intermediately basic functional groups and the weakly acidic functional groups can be changed optionally. Most suitable proportions can be selected depending on the amount of monomethyl adipate and the amount of alkali metal ions to be adsorbed and removed.

When monomethyl adipate and alkali metal ions are to be adsorbed on the amphoteric ion exchange resin having weakly or intermediately basic functional groups and weakly acidic functional groups, the presence of methanol may prevent the weakly or intermediately basic functional groups from adsorbing monomethyl adipate. Therefore, in order to adsorb and separate monomethyl adipate and alkali metal ions at the same time, it is necessary to control the presence of methanol as low as possible. Generally, it is preferable to control the concentration of methanol in the feeding solution to the fixed bed packed with the amphoteric ion exchange resin and in the remaining solution in the fixed bed less than 5% by weight. Therefore, in this case, the removal of methanol from the electrolytic solution should be conducted before passing to the fixed bed.

As a regenerant of the amphoteric ion exchange resin, there may be used water or hydrophilic organic solvents such as methanol, ethanol, acetone, tetrahydrofuran, and the like. Among them, methanol is preferable industrially, since the methanol removed from the electrolytic solution can be used. As to a regeneration temperature, higher temperatures are preferable from the viewpoint of regeneration efficiency, but taking a boiling point of a regenerant and heat resistance of the resin into consideration, a temperature between room temperature and 60° C. is generally preferable.

When removal of methanol is carried out before ion exchange of anions and cations and the methanol is used for regeneration of the ion exchange resin, it is necessary to remove the regenerant remaining in the ion exchange resin by pushing out after regeneration of the ion exchange resin. As a pushing out solution, there may be used water or an organic compound having no affinity to water and being not adsorbed on the resin such as dimethyl adipate, dimethyl sebacate, or the like. Industrially preferable one is an electrolytic solution from which methanol, monomethyl adipate and its metal salt are removed, taking aftertreatments into consideration. In the case of carrying out the anion exchange treatment in combination with the water treatment, water can be used as a pushing out solution.

The process for separating and purifying dimethyl sebacate from the electrolytic solution containing dimethyl sebacate will further be explained hereinafter referring to the schematic flow diagrams of the attached drawings, wherein substitution step of a regenerant solution remaining in an ion exchange resin column is omitted.

Figure 3:
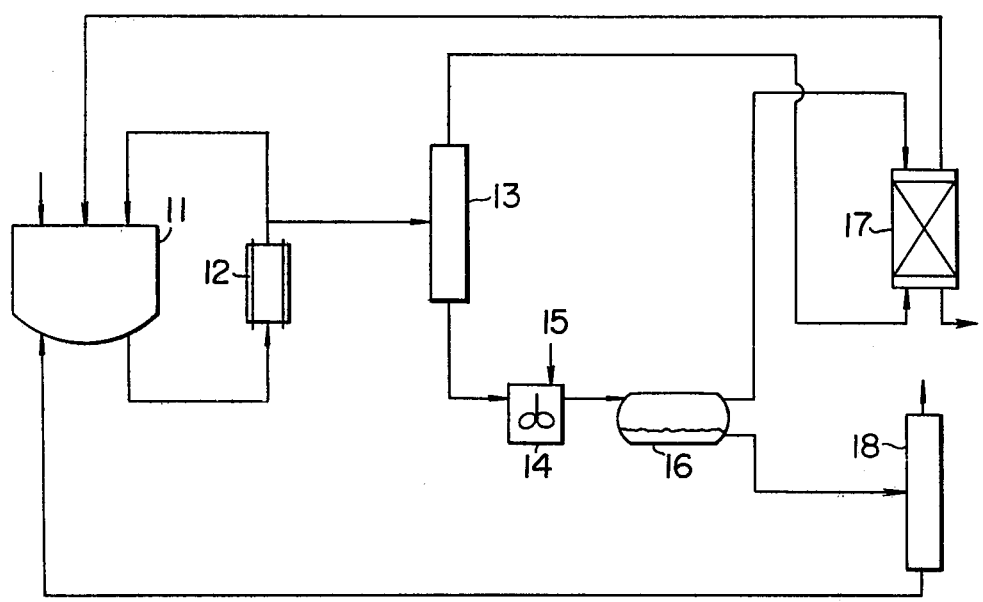
FIG. 3 is a schematic flow diagram suitable for practicing the second step of this invention, wherein removal of methanol from the electrolytic solution, water treatment and anion exchange treatment by a fixed bed are conducted in this order.

FIG. 3 is a flow sheet showing one example of the water treatment and the anion exchange treatment on a fixed bed. The electrolytic solution is recycled between an electrolytic solution tank 11 and an electrolytic cell 12. A part of the electrolytic solution in the electrolytic cell 12 is taken out and passes to a distillation column 13. In the distillation column 13, methanol is removed and the remaining solution passes to a mixer 14 from the bottom of the column 13. Water is fed from an inlet 15 and mixed with the remaining solution with sufficient agitation and subsequently the mixture passes to a decanter 16. From the top of decanter 16, an oil layer containing dimethyl sebacate and monomethyl adipate is taken out and passes to the top of an anion exchange resin column 17. In the anion exchange resin column 17, monomethyl adipate is adsorbed on the resin and a solution containing as a major component dimethyl sebacate is taken out of the bottom of the column 17 to give highly pure dimethyl sebacate by further distillation. The methanol removed by distillation from the top of the distillation column 13 passes to the bottom of anion exchange resin column 17 to recover the monomethyl adipate adsorbed on the resin and then is recycled to the electrolytic solution tank 11 to be fed to the electrolytic reaction. From the bottom of decanter 16, an aqueous layer containing an alkali metal salt of monomethyl adipate is taken out. The aqueous layer is separated into water and the alkali metal salt of monomethyl adipate in an evaporator 18. The water is reused for extraction and the alkali metal salt of monomethyl adipate is recycled to the electrolytic solution tank 11 to be fed to the electrolytic reaction.

Figure 4:
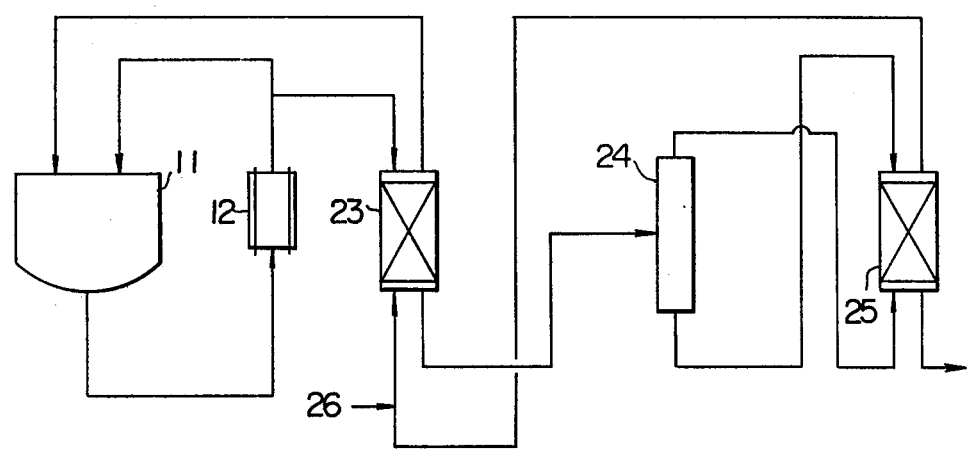
FIG. 4 is a schematic flow diagram suitable for practicing the second step of this invention, wherein cation exchange treatment by a fixed bed followed by gradual anion exchange treatment are conducted.

FIG. 4 is a flow sheet showing one example of the cation exchange treatment on a fixed bed and the anion exchange treatment on a fixed bed wherein the former is carried out gradually before the latter. The electrolytic solution is recycled between an electrolytic solution tank 11 and an electrolytic cell 12. A part of the electrolytic solution in the electrolytic cell 12 is taken out and passes to the top of a cation exchange resin column 23. In the cation exchange resin column 23, the alkali metal ions are adsorbed on the resin and the electrolytic solution from which the alkali metal ions are removed is taken out of the bottom of the column 23 and passes to a distillation column 24. In the distillation column 24, methanol is removed and the remaining solution is taken out of the bottom of the column 24 and passes to the top of an anion exchange resin column 25. In the anion exchange resin column 25, monomethyl adipate is adsorbed on the resin and a solution containing as a major component dimethyl sebacate is taken out of the bottom of the column 25 to give highly pure dimethyl sebacate by further distillation. The methanol removed by distillation from the top of the distillation column 24 passes to the bottom of the anion exchange resin column 25 to recover the monomethyl adipate adsorbed on the resin therein and is taken out of the top of column 25. To the bottom of cation exchange resin column 23, monomethyl adipate the amount of which corresponds to that consumed in the electrolytic reaction is fed from an inlet 26 and the methanol solution containing monomethyl adipate taken out of the top of the anion exchange resin column 25 is also fed, and then the alkali metal ions adsorbed on the resin are recovered in the solution. A methanol solution containing monomethyl adipate and its alkali metal salt is taken out of the top of the column 23 and recycled to the electrolytic solution tank 11 to be fed to the electrolytic reaction.

Figure 5:
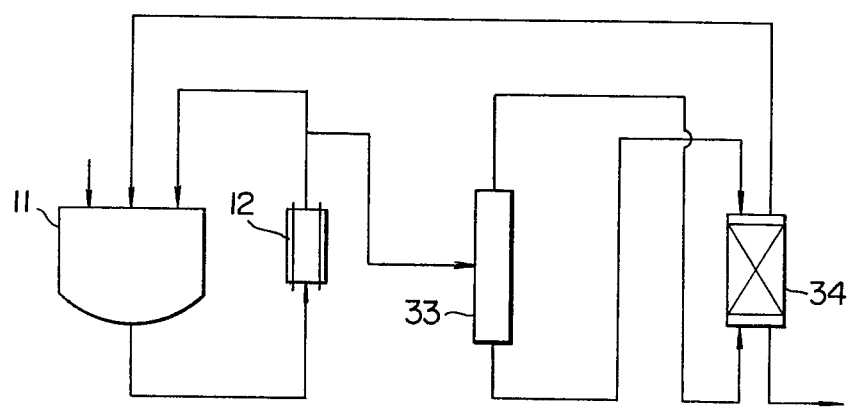
FIG. 5 is a schematic flow diagram suitable for practicing the second step of this invention, wherein cation exchange treatment and anion exchange treatment are conducted simultaneously.

FIG. 5 is a flow sheet showing one example of the cation exchange treatment on a fixed bed and the anion exchange treatment on a fixed bed wherein the both treatments are carried out at the same time. The electrolytic solution is recycled between an electrolytic solution tank 11 and an electrolytic cell 12. A part of the electrolytic solution in the electrolytic cell 12 is taken out and passes to a distillation column 33. In the distillation column 33, methanol is removed and the remaining solution is taken out of the bottom of the column 33 and passes to the top of an ion exchange resin column 34. In the ion exchange resin column 34, monomethyl adipate and alkali metal ions are adsorbed on the amphoteric ion exchange resin and a solution containing as a major component dimethyl sebacate is taken out of the bottom of the column 34 to give highly pure dimethyl sebacate by further distillation. The methanol removed by distillation from the top of the distillation column 33 passes to the bottom of the ion exchange resin column 34, in which the monomethyl adipate and alkali metal ions adsorbed on the resin are recovered in the methanol. The methanol solution containing monomethyl adipate and its alkali metal salt is taken out of the top of the column 34 and recycled to the electrolytic solution tank 11 to be fed to the electrolytic reaction.

Since readsorption of an ion exchange resin after regeneration is possible as shown in the working examples mentioned hereinafter, continuous operations of ion exchange resin columns are apparently possible.

As mentioned above, according to this invention, separation of dimethyl sebacate from the electrolytic solution without accompanying monomethyl adipate and its alkali metal salt becomes possible by combining the water treatment and the anion exchange treatment or by combining the cation exchange treatment and the anion exchange treatment in the separation of dimethyl sebacate from the electrolytic solution containing dimethyl sebacate. Further, by-products such as dimethyl adipate, methyl n-valerate, methyl ω-hydroxyvalerate, methyl allylacetate and the like accompanied to dimethyl sebacate can be separated, for example, by distillation. Thus, contrary to a conventional extracting separation method of using more than a certain amount of water and an organic solvent not present in the system in order to obtain highly pure dimethyl sebacate, the process of this invention can produce extremely highly pure dimethyl sebacate without introducing an organic solvent and water into the system, or in some cases by only introducing a very small amount of water into the system in order to extract an alkali metal salt of monomethyl adipate.

Hydrolysis of dimethyl sebacate separated and purified in the second step to sebacic acid in the third step of this invention will be explained in detail below.

As a reaction form of the hydrolysis, a continuous reaction is disadvantageous and a batch reaction is advantageous economically in order to complete the reaction without admixing unreacted materials such as monomethyl sebacate and to heighten quality of sebacic acid.

The hydrolysis reaction can be carried out using as a catalyst a mineral acid such as nitric acid, sulfuric acid, hydrochloric acid, or the like or an organic sulfonic acid such as p-toluenesulfonic acid or the like. The use of nitric acid as a catalyst is preferable from the viewpoint of corrosion of materials for the reactor and the like and the reaction rate. In this case, when dimethyl sebacate is added to an acid catalyst aqueous solution of 10 to 30% by weight concentration in an amount of less than the amount corresponding to the saturated solubility of sebacic acid in the acid catalyst aqueous solution at the hydrolysis temperature and the hydrolysis is carried out while removing methanol, the hydrolysis can be completed very rapidly. It is also possible to carry out the hydrolysis reaction by using water initially and subsequently by using an aqueous nitric acid solution. In this case, the hydrolysis by using water can be carried out by adding water four times or more as much as the weight of dimethyl sebacate at a temperature of 220° to 280° C. for 2 to 5 hours under a pressure of 35 to 50 atmospheres, and the hydrolysis by using the aqueous nitric acid solution can be carried out with a nitric acid concentration of 12 to 25% by weight at a temperature of 80° to 100° C. for 0.5 to 1.5 hours. Further, in order to accelerate the hydrolysis reaction rate, it is also possible to carry out the hydrolysis reaction while adding sebacic acid which is a reaction product to the system and removing the methanol produced by the reaction out of the system. Comparing with the method of using nitric acid as a catalyst, this method has an disadvantage in that the reaction rate is not so fast, but has many advantages in that the reaction can be carried out at a relatively low temperature, the reaction can be completed by one step while maintaining the reaction rate over a certain standard, separation of the catalyst from the produced sebacic acid is easy, and methanol is not modified. In the case of using nitric acid as a catalyst, the methanol produced in the reaction solution reacts with nitric acid to produce methyl nitrate and this cannot be completely prevented even if the reaction is carried out while removing the methanol out of the system. Further, if the first half of the reaction is carried out without using catalyst, sebacic acid produced is slightly or considerably colored. If such a reaction is carried out at high temperatures and high pressures, coloration of the reaction product increases remarkably. Taking the above-mentioned points into consideration, the method of adding sebacic acid to the reaction system while removing the methanol produced thereby from the reaction system during the hydrolysis is the most preferable method in industrial production of sebacic acid by hydrolysis of dimethyl sebacate.

The effect of adding sebacic acid in order to accelerate the hydrolysis reaction is remarkable in the first half of the reaction, wherein there are two layers, i.e. a dimethyl sebacate layer and a water layer. As shown in Table 3 mentioned hereinafter, with an increase of an adding amount of sebacic acid, a time required for making the reaction solution uniform is shortened and the reaction is accelerated. But since the addition of an excess amount of sebacic acid lowers volume efficiency of the reactor, it is preferable to add sebacic acid in a proportion of 1 to 20% by weight based on the weight of dimethyl sebacate in industrial production.

In order to accelerate the hydrolysis reaction other than the addition of sebacic acid to the system, it is preferable to carry out the reaction while removing the methanol produced by the hydrolysis out of the system continuously by evaporation and at the same time continuously supplementing water which is removed together with the methanol. Further, this procedure makes it possible to complete the reaction. Removal of methanol can be conducted immediately after the reaction, but the effect is more remarkable in the latter half of the reaction in which the reaction solution is present as a uniform solution than in the first half of the reaction in which two layers, i.e. a dimethyl sebacate layer and a water layer, are present as an ununiform solution. Further, if methanol is removed in the first half of the reaction, a considerable amount of dimethyl sebacate is also distilled off together with methanol, which makes it necessary to separate and recover the dimethyl sebacate distilled. Taking these facts into consideration, it is preferable to remove methanol in the latter half of the reaction. Removal of methanol by evaporation out of the system accompanys removal of water. Much more amounts of evaporating removal of methanol and water are preferable from the viewpoint of the reaction rate, but too much amounts of removal of methanol and water make the thermal load larger. Therefore, removal of usually 2 to 6 parts by weight of the methanol and water based on 1 part by weight of dimethyl sebacate charged is preferable. As to a water concentration in the reaction solution, higher concentration is preferable from the viewpoint of the reaction rate, but lower one is preferable from the viewpoint of volume efficiency of the reactor. Usually, it is preferable to maintain the water concentration in the range of 10 to 75% by weight during the hydrolysis reaction.

As to a reaction temperature, higher reaction temperatures are desirable from the viewpoint of the reaction rate, but higher reaction temperatures require higher reaction pressures and further cause coloration of the reaction product. Particularly, a reaction temperature over 220° C. causes remarkable coloration of the reaction product. In the first half of the reaction in which the reaction solution is present as an ununiform solution, effect of the reaction temperature is very great as shown in Table 5 mentioned hereinafter, and the reaction rate is considerably slow at temperatures below 180° C. In the latter half of the reaction in which the reaction solution is present as a uniform solution, effect of the reaction temperature is little, and there is almost no difference over 150° C. Taking these facts into consideration, it is preferable to carry out the reaction at a temperature of 180° to 220° C. in the first half of the reaction in which the reaction solution is present as an ununiform solution, and at a temperature of 150° to 220° C. in the latter half of the reaction in which the reaction solution is present as a uniform solution.

A concrete example of a process of hydrolysis of dimethyl sebacate while adding sebacic acid to the reaction system and removing methanol produced by the reaction out of the system is as follows.

In a batch type reactor, dimethyl sebacate, sebacic acid and water are placed and the hydrolysis is started. Until the reaction solution becomes uniform, heating is continued. At a time when the reaction solution becomes uniform, methanol and water are removed out of the reactor continuously by evaporation, while at the same time insufficient water which is caused by removal together with methanol is supplemented continuously to complete the reaction. The aqueous solution containing methanol removed out of the reactor passes to a distillation column, from the top of which methanol is distilled and recovered, while from the bottom of which water is taken off and passes to the reactor continuously. After the reaction, activated carbon is charged into the reactor to decolor the reaction solution, and subsequently the aqueous solution containing activated carbon and sebacic acid is taken out of the reactor and passes to a filter. After filtering the activated carbon, the aqueous solution containing sebacic acid passes to an evaporator, in which water is removed by evaporation and recovered to give sebacic acid.

This invention will be explained in detail by way of the following examples, in which all percents and parts are by weight unless otherwise specified.

EXAMPLE 1

A starting material solution was prepared so as to contain 34.7% of adipic acid, 37.3% of dimethyl adipate, 15.2% of methanol and 12.8% of water. A strongly acidic cation exchange resin (Diaion PK208, a trade name, manufactured by Mitsubishi Chemical Industries Ltd.) regenerated to the H type, 100 ml (based on water standard), was substituted with water and packed in a jacketed column of inner diameter of 15 mm and 1000 mm long. Warm water of 80° C. was passed through the jacket. 1 Kg of the starting material solution preheated at 80° C. was passed through the column downwardly at a flow rate of SV 3. A first 400 g of effluent was removed as a first stream and a sample was taken out of the rest of the effluent as a reaction solution. After analyzing by gas chromatography, the reaction solution was found to have 32.0% of monomethyl adipate and 35.1% of dimethyl adipate. Separation and purification of monomethyl adipate from the reaction solution was carried out by distillation.

An electrolytic solution for electrolytic condensation was prepared by dissolving monomethyl adipate obtained by the half esterification of adipic acid, potassium hydroxide and dimethyl sebacate in methanol so as to contain 4% of monomethyl adipate, 4.6% of potassium salt of monomethyl adipate, 20% of dimethyl sebacate and 0.5% of water in methanol. 2 Kg of the electrolytic solution was placed in an electrolytic solution tank and recycled to an electrolytic cell. In the electrolytic cell, between cathode and anode, each having electricity passing area of 1.5 cm×100 cm, there was placed a polyethylene plate of 1 mm thick having an opening zone so as to make electricity passing area 1.5 cm×100 cm and the distance between each electrode was determined to be 1 mm. The cathode was a titanium plate of 2 mm thick and the anode was a titanium plate of 2 mm thick plated with platinum of 2 microns thick. The electrolytic cell had an inlet and an outlet of the electrolytic solution. The electrolysis was conducted by passing the electrolytic solution between the both electrodes at a flow rate of 2 m/sec, with current density of 10 A/dm$^2$, at an electrolytic solution temperature of 55° C. and by adding continuously monomethyl adipate which was consumed with the proceeding of electrolysis for 3 hours. Electrolytic cell voltage was 7.8 volts. After the electrolysis, an yield amount of dimethyl sebacate was obtained by gas chromatography. Current efficiency was 67.8% and material yield was 80.9%.

The electrolytic solution obtained by the electrolytic condensation was a methanol solution containing 4% of monomethyl adipate, 4.6% of potassium salt of monomethyl adipate, 24% of dimethyl sebacate, and trace amounts of by-products of dimethyl adipate, methyl n-valerate, methyl ω-hydroxyvalerate, methyl allylacetate and the like. The methanol was removed from the electrolytic solution by distillation so as to reduce the concentration to 2.5%.

To 250 g of the electrolytic solution from which methanol had been removed, 25 g of water was added and stirred at room temperature. Consequently, the solution was separated into two layers, the upper layer being an oil layer containing dimethyl sebacate and monomethyl adipate and the lower layer being a water layer containing potassium salt of monomethyl adipate. Methanol concentration in the oil layer was 1.5%.

In the next place, 100 ml (based on water standard) of a tertiary amine type weakly basic anion exchange resin (Diaion WA-30, a trade name, manufactured by Mitsubishi Chemical Industries Ltd.) regenerated to the OH type was substituted with the electrolytic solution from which methanol, monomethyl adipate and its potassium salt had been removed and packed in a jacketed column of inner diameter of 15 mm and 1000 mm long. 200 Grams of the oil layer from which methanol and potassium salt of monomethyl adipate had been removed was passed through the anion exchange resin column downwardly at a flow rate of SV 1.0 at room temperature. The amount of effluent in which the concentration of monomethyl adipate was 0.05% or less (this concentration being defined as a concentration of monomethyl adipate at a break through point) was 165 g and break through capacity was 0.71 meq/ml-resin. Break through capacity of monomethyl adipate was obtained by the following equation:

$$\text{Break through capacity} = \frac{(W_A - W_B) C_A}{M_A V_A (100 - C_A)} \times 1000$$

wherein $W_A$ is the effluent amount flown out until the break through point (grams), $W_B$ is the amount of the solution which substitutes the resin (grams), $C_A$ is the concentration of monomethyl adipate in the feeding solution to the anion exchange resin column (percents), $M_A$ is the molecular weight of monomethyl adipate, and $V_A$ is the volume of the resin (based on water standard) (ml). (Break through capacity is obtained in the same manner as mentioned above in the case of other anion exchange resin treatments).

Through the jacket of the anion exchange resin column, warm water of 60° C. was passed continuously, and 250 ml of methanol preheated at 60° C. was passed through the anion exchange resin column upwardly at a flow rate of SV 1.5 to push out the remaining solution in the anion exchange resin column and to desorb the monomethyl adipate adsorbed on the resin. Recovered amount of monomethyl adipate in the effluent was 17 g, which was 81% in recovery percent. Recovery percent was calculated according to the following equation:

$$\text{Recovery percent} = \frac{W_C - W_D}{W_E} \times 100$$

wherein $W_C$ is the amount of monomethyl adipate recovered in the effluent (grams), $W_D$ is the amount of monomethyl adipate in the remaining solution in the anion exchange resin column (grams), and $W_E$ is the amount of monomethyl adipate adsorbed on the resin (grams). (Hereinafter, recovery percent is obtained in the same manner as mentioned above in the case of other anion exchange resin treatments).

Then, the anion exchange resin column was cooled to room temperature and 150 g of the electrolytic solution from which methanol, monomethyl adipate and its potassium salt had been removed was passed through the anion exchange resin column upwardly at room temperature at a flow rate of SV 1.5 to push out the methanol. The methanol concentration in the effluent was reduced to 4.5% by weight.

The above-mentioned oil layer from which methanol and potassium salt of monomethyl adipate had been removed in an amount of 200 g was passed through the anion exchange resin column downwardly at room temperature at a flow rate of SV 1.0 again. Effluent amount flown out until the break through point of monomethyl adipate was 166 g and break through capacity was 0.72 meq/ml-resin.

In the adsorption procedure and readsorption procedure of the anion exchange treatment, purity of dimethyl sebacate in the effluent from the anion exchange resin column flown out until the break through point of monomethyl adipate was 99.9% or more. Purity of dimethyl sebacate was calculated according to the following equation:

$$\text{Purity} = \frac{C_C}{C_B + C_C} \times 100$$

wherein $C_B$ is the concentration of monomethyl adipate, and $C_C$ is the concentration of dimethyl sebacate. Analysis of monomethyl adipate and dimethyl sebacate was carried out by gas chromatography. Further, separation and purification of dimethyl sebacate from the effluent from the anion exchange resin column flown out until the break through point of monomethyl adipate was conducted by distillation.

A mixture of 190 g of dimethyl sebacate separated and purified from the electrolytic solution obtained by the electrolytic condensation, 9 g of sebacic acid and 200 g of water was placed in a 1 liter autoclave. The reaction was carried out at a temperature of 180° C. with vigorous stirring. The reaction solution was initially ununiform but became uniform after 3.0 hours from the beginning of the reaction. When the reaction solution became uniform, methanol and water began to be removed continuously from the autoclave and at the same time insufficient water caused by the removal of water together with methanol was supplemented continuously to the autoclave, and under such conditions the reaction was continued for an additional 5 hours. Total amount of methanol and water removed was 640 g and total water supplemented was 660 g. During the reaction, inner pressure of the autoclave was 7 to 9 kg/cm² (gauge). Conversion by hydrolysis after the reaction was 99.3% by mole. The conversion by hydrolysis was calculated as a ratio of molar number of sebacic acid produced to molar number of dimethyl sebacate charged.

EXAMPLE 2

From a starting material solution (solution A) containing 56.3% of adipic acid, 20.1% of dimethyl adipate, 12.1% of methanol and 11.4% of water, adipic acid was deposited below 90° C. The solution A was placed in an autoclave and heated at 150° C. to carry out the reaction for 4 hours to give a reaction solution (solution B). The composition of solution B was 21.6% of adipic acid, 38.0% of monomethyl adipate, 20.3% of dimethyl adipate, 4.4% of methanol and 15.6% of water. A mixture of 1 part of the solution A and 4 parts of the solution B was prepared as a feeding starting material solution to an ion exchange resin column. The composition of the mixture was 28.5% of adipic acid, 30.4% of monomethyl adipate, 20.1% of dimethyl adipate, 5.9% of methanol and 14.8% of water, with a dissolving temperature of adipic acid of 73° C.

Then, 100 ml (based on water standard) of a strongly acidic cation exchange resin (Amberlite 200 C, a trade name, manufactured by Rohm & Haas Co.) regenerated to the H type was substituted with water and packed in a Jacketed column of inner diameter of 15 mm and 1000 mm long. Warm water of 80° C. was passed through the jacket. Subsequently, 2 kg of the feeding starting material solution preheated at 80° C. was passed through the ion exchange resin column downwardly at a flow rate of SV 8. A first 400 g of effluent was removed as a first stream and a sample was taken out of the rest of the effluent as a reaction solution. After analyzing by gas chromatography, the reaction solution was found to contain 39.5% of monomethyl adipate, and 20.1% of dimethyl adipate. Separation and purification of monomethyl adipate from the reaction solution was carried out by distillation.

An electrolytic solution for electrolytic condensation was prepared by dissolving monomethyl adipate obtained by the half esterification of adipic acid, sodium methylate, and dimethyl sebacate in methanol so as to contain 4.5% of sodium salt of monomethyl adipate and 20% of dimethyl sebacate in methanol. Electrolytic condensation was conducted in the same manner as described in Example 1 except for making the water concentration in the electrolytic solution 1.51% by adding water to the electrolytic solution. Electrolytic cell voltage was 7.8 volts. After the electrolysis, yielded amount of dimethyl sebacate was obtained by gas chromatography. Current efficiency was 66.5% and material yield was 79.3%.

The electrolytic solution obtained by the electrolytic condensation was a methanol solution containing 4% of monomethyl adipate, 4.5% of sodium salt of monomethyl adipate, 24% of dimethyl sebacate, and trace amounts of by-products of dimethyl adipate, methyl n-valerate, methyl ω-hydroxyvalerate, methyl allylacetate and the like. The methanol was removed from the electrolytic solution by distillation so as to reduce the concentration to 2.5%.

To 250 g of the electrolytic solution from which methanol had been removed, 25 g of water was added and stirred at room temperature. Consequently, the solution was separated into two layers, the upper layer being an oil layer containing dimethyl sebacate and monomethyl adipate and the lower layer being a water layer containing sodium salt of monomethyl adipate. Methanol concentration in the oil layer was 1.5%.

Anion exchange treatment was conducted in the same manner as described in Example 1 except for changing the regeneration temperature from 60° C. to 30° C. The results were as follows:

(1) During the adsorption procedure, effluent amount flown out until the break through point of monomethyl adipate was 166 g and break through capacity was 0.72 meq/ml-resin. Purity of dimethyl sebacate in the effluent was 99.9% or more.

(2) During the regeneration procedure, the amount of monomethyl adipate recovered in the effluent was 16 g, which was 70% in recovery percent.

(3) During the readsorption procedure, effluent amount flown out until the break through point of monomethyl adipate was 158 g and break through capacity was 0.66 meq/ml-resin. Purity of dimethyl sebacate in the effluent was 99.9% or more.

Separation and purification of dimethyl sebacate from the effluent from the anion exchange resin column flown out until the break through point of monomethyl adipate was conducted by distillation.

A mixture of 80% of dimethyl sebacate separated and purified from the electrolytic solution obtained by the electrolytic condensation, 2% of sebacic acid and 18% of water in an amount of 400 g was placed in a 1 liter autoclave. The reaction was carried out at a temperature of 180° C. with vigorous stirring. After 3.7 hours from the beginning of the reaction, the reaction solution became a uniform solution. The latter half of the reaction after the reaction solution had become a uniform solution was carried out in the same manner as described in Example 1. Total amount of methanol and water removed by distillation until the end of the reaction was 920 g and total water supplemented was 970 g. Conversion by hydrolysis after the reaction was 98.9% by mole.

EXAMPLE 3

Using a three-necked glass flask equipped with a thermometer, a condenser and a stirrer, a reaction solution containing 146 g of adipic acid, 32 g of methanol, 36 g of water and 50 milligram equivalents of nitric acid was refluxed for 6 hours under atmospheric pressure with heating using an oil bath. After the reaction, it was found by gas chromatographic analysis that the resulting solution contained 114 g of monomethyl adipate and 24.5 g of dimethyl adipate. Separation and purification of monomethyl adipate from the resulting solution was conducted by distillation.

The electrolytic condensation was conducted in the same manner as described in Example 2 except for changing the neutral salt group from sodium methylate to sodium carbonate by using monomethyl adipate obtained by the half esterification of adipic acid. Electrolytic cell voltage was 7.8 volts. Current efficiency was 67.2% and material yield was 80.2%.

From the electrolytic solution obtained by the electrolytic condensation, removal of methanol and separation by extraction of sodium salt of monomethyl adipate to a water layer were conducted in the same manner as described in Example 1.

In the next place, 100 ml (based on water standard) of a tertiary amine type weakly basic anion exchange resin (Diaion WA-30, a trade name, manufactured by Mitsubishi Chemical Industries Ltd.) regenerated to the OH type was substituted with water and packed in a jacketed column of inner diameter of 15 mm and 1000 mm long. 195 Grams of the oil layer from which metanol and sodium salt of monomethyl adipate had been removed was passed through the anion exchange resin column downwardly at room temperature at a flow rate of SV 1.0. The effluent was separated into two layers, the upper layer being an oil layer containing dimethyl sebacate and the lower layer being a water layer. Effluent amount of the oil layer flown out until the break through point of monomethyl adipate was 100 g and break through capacity was 0.73 meq/ml-resin. Purity of dimethyl sebacate in the oil layer was 99.9% or more.

Pushing out of the remaining solution in the anion exchange resin column and desorption of the monomethyl adipate adsorbed on the resin were conducted in the same manner as described in Example 1. The amount of monomethyl adipate recovered in the effluent was 17 g, which was 80% in recovery percent.

After cooling the anion exchange resin column to room temperature, 150 ml of water at room temperature was passed through the anion exchange resin column upwardly at a flow rate of SV 1.5 to push out the methanol. Concentration of methanol in the effluent was reduced to 0.1%.

Subsequently, 195 g of the oil layer from which methanol and sodium salt of monomethyl adipate had been removed was passed through the anion exchange resin column downwardly at room temperature at a flow rate of SV 1.0 again. The effluent was separated into two layers, the upper layer being an oil layer containing dimethyl sebacate and the lower layer being a water layer. Effluent amount of the oil layers flown out until the break through point of monomethyl adipate was 101 g and break through capacity was 0.73 meq/ml-resin. Purity of dimethyl sebacate in the oil layer was 99.9% or more. Separation and purification of dimethyl sebacate from the effluent from the anion exchange resin column flown out until the break through point of monomethyl adipate was conducted by distillation.

In a 2 liter glass vessel, 100 g of dimethyl sebacate separated and purified from the electrolytic solution obtained by the electrolytic condensation and 1.5 kg of a 18% aqueous solution of nitric acid were placed and refluxed under atmospheric pressure with vigorous stirring for 3 hours while removing methanol by distillation to carry out the hydrolysis. Conversion by hydrolysis after the reaction was 99.9% by mole. The methanol concentration during the hydrolysis was maintained at 0.03% or less and sebacic acid produced by the hydrolysis was dissolved in the reaction solution and not deposited.

EXAMPLE 4

A mixture of 146 g of adipic acid, 96 g of methanol, 54 g of water and 139 g of dimethyl adipate was placed in an autoclave and reacted at a temperature of 150° C. for 2 hours with vigorous stirring. After the reaction, it was found by gas chromatographic analysis that 112 g of monomethyl adipate was produced. Separation and purification of monomethyl adipate from the reaction solution was conducted by distillation.

The electrolytic condensation was conducted in the same manner as described in Example 2 except for changing the neutral salt group from sodium methylate to sodium bicarbonate by using monomethyl adipate obtained by the half esterification of adipic acid. Electrolytic cell voltage was 7.8 volts. Current efficiency was 67.0% and material yield was 79.8%.

Separation of dimethyl sebacate from the electrolytic solution obtained by the electrolytic condensation was conducted in the same manner as described in Example 3 except for changing the temperature of water passing through the jacket of the anion exchange resin column from 60° C. to 90° C. and changing the regenerant from methanol of 60° C. to hot water of 90° C. The results were as follows:

(1) During the adsorption procedure, effluent amount of the oil layer flown out until the break through point of monomethyl adipate was 102 g and break through capacity was 0.75 meq/ml-resin. Purity of dimethyl sebacate in the oil layer was 99.9% or more.

(2) During the regeneration procedure, the amount of monomethyl adipate recovered in the effluent was 16 g, which was 70% in recovery percent.

(3) During the readsorption procedure, effluent amount of the oil layer flown out until the break through point of monomethyl adipate was 89 g and break through capacity was 0.65 meq/ml-resin. Purity of dimethyl sebacate in the oil layer was 99.9% or more.

Separation and purification of dimethyl sebacate from the effluent from the anion exchange resin column flown out until the break through point of monomethyl adipate was conducted by distillation.

Hydrolysis of dimethyl sebacate separated and purified from the electrolytic solution obtained by the electrolytic condensation was conducted in the same manner as described in Example 1.

EXAMPLE 5

Production of monomethyl adipate by the half esterification of adipic acid was conducted using the flow sheet of FIG. 1.

Figure 2:
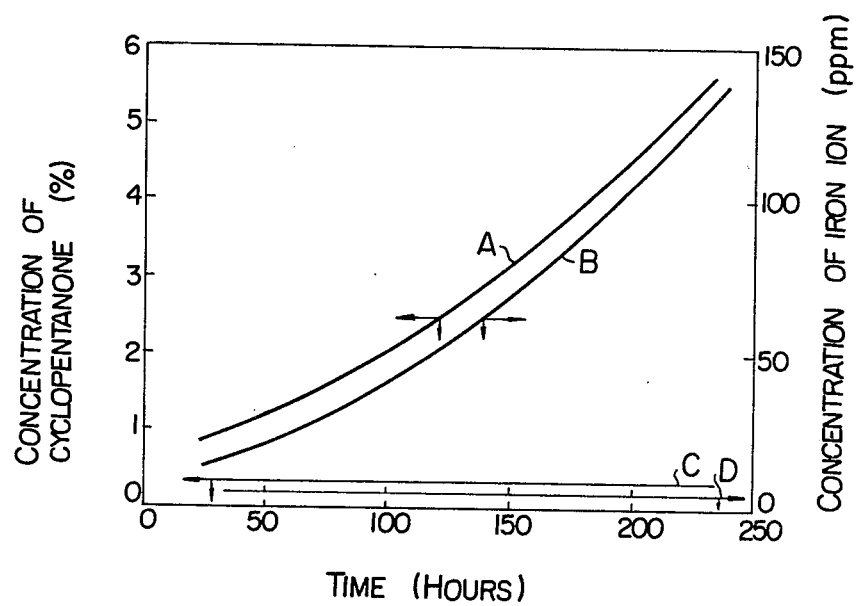
FIG. 2 graphically shows the relationship between iron ion concentration or cyclopentanone concentration in the reaction solution and the lapse of time in the first step of this invention as disclosed in Examples 5 and 6.

From the inlet 7, adipic acid and methanol were fed at a rate of 13.8 kg/hr and 3.0 kg/hr, respectively, to the dissolving vessel 1. Methanol and water, dimethyl adipate and water, adipic acid and monomethyl adipate, and a part of the reaction solution taken out of the top of distillation column 4, out of the top of distillation column 5, out of the bottom of distillation column 6 and out of the drain 8, respectively, were recycled. The dissolving vessel 1 was heated to 80° C. and a starting material solution was taken out of the vessel 1 at a rate of 240 kg/hr and passed to the top of ion exchange resin column 2. The composition of the starting material solution was 28.0% of adipic acid, 20.3% of dimethyl adipate, 30.8% of monomethyl adipate, 5.7% of methanol, 14.9% of water and 0.3% of cyclopentanone. The ion exchange resin column 2 was packed with 15 l. of strongly acidic cation exchange resin (Amberlite 200 C, a trade name, manufactured by Rohm & Haas Co.) regenerated to the H type and the starting material solution was passed therethrough maintaining at 80° C. The resin in the ion exchange resin column 2 was regenerated with 1 N nitric acid aqueous solution at a rate of one time after continuous 200 hours' operation. The effluent taken out of the bottom of the ion exchange resin column 2 was fed to the top of the ion exchange resin column 3. The ion exchange resin column 3 was packed with 60 l. of strongly acidic cation exchange resin (Amberlite 200 C) regenerated to the H type and the effluent from the bottom of the ion exchange resin column 2 was passed therethrough maintaining at 80° C. From the bottom of the ion exchange resin column 3, the reaction solution was taken out at a rate of 240 kg/hr and passed to the distillation column 4 in an amount of ¼ of the solution, while ¾ of the solution was recycled to the dissolving vessel 1 through the drain 8. The composition of the reaction solution taken out of the bottom of ion exchange resin column 3 was 22.0% of adipic acid, 20.2% of dimethyl adipate, 37.4% of monomethyl adipate, 4.3% of methanol, 15.7% of water and 0.3% of cyclopentanone. Changes of concentrations of iron ion and cyclopentanone in the solution taken out of the ion exchange resin column 3 with the lapse of time were as shown in Table 1 and FIG. 2. In FIG. 2, the curve C indicates cyclopentanone and the curve D iron ion. In the distillation column 4, the temperature at the bottom was maintained at 140° C. under atmospheric pressure and methanol and water were removed by distillation from the top of the column and passed to the dissolving vessel 1, while the remaining solution was taken out of the bottom of the column and passed to the distillation column 5. In the distillation column 5, the temperature at the bottom was maintained at 200° C. under reduced pressure (20 mmHg) and dimethyl adipate and water were removed by distillation from the top of the column. The dimethyl adipate and water taken from the top of the distillation column 5 were separated into two layers, and the water was taken out of the drain 9 at a rate of 2.0 kg/hr while the remaining solution was recycled to the dissolving vessel 1. From the bottom of the distillation column 5, a solution containing adipic acid and monomethyl adipate was taken out and passed to the distillation column 6. In the distillation column 6, the temperature at the bottom was maintained at 210° C. under reduced pressure (20 mmHg) and monomethyl adipate was obtained from the top of the column at a rate of 15 kg/hr in order to produce an electrolytic solution used for the electrolytic condensation. From the bottom of the distillation column 6, a solution containing adipic acid and monomethyl adipate was taken out and recycled to the dissolving vessel 1.

As to materials of each apparatus, the dissolving vessel 1 was made of SUS 304, the ion exchange resin columns 2 and 3 were made of SUS 304, the distillation column 4 was made of SUS 304, the distillation column 5 was made of SUS 316, and as to the distillation column 6, the reboiler was made of titanium and the body was made of SUS 316.

TABLE 1

| Lapse of time (hours) | Concentration of cyclopentanone (%) | Concentration of iron ion (ppm) |
|---|---|---|
| 50 | 0.3 | 5 |
| 100 | 0.3 | 5 |
| 150 | 0.3 | 5 |
| 200 | 0.3 | 5 |

Using monomethyl adipate obtained by the half esterification of adipic acid, the electrolytic condensation was conducted in the same manner as described in Example 1.

From the electrolytic solution obtained by the electrolytic condensation, removal of methanol and separation by extraction of potassium salt of monomethyl adipate to water layer were conducted in the same manner as described in Example 1.

In the next place, 100 ml (based on water standard) of a pyridinium type strongly basic anion exchange resin (Bio-Rex 9, a trade name, manufactured by Bio-Rad Co.) regenerated to the OH type was substituted with the electrolytic solution from which methanol, monomethyl adipate and its potassium salt had been removed and packed in a column of inner diameter of 12 mm and 1500 mm long. Then, 400 g of the oil layer from which methanol and potassium salt of monomethyl adipate had been removed was passed through the anion exchange resin column downwardly at room temperature at a flow rate of SV 1.0. Effluent amount flown out until the break through point of monomethyl adipate was 218 g and break through capacity was 1.10 meq/ml-resin. Purity of dimethyl sebacate in the effluent was 99.9% or more.

Pushing out of the remaining solution in the anion exchange resin column and desorption of the monomethyl adipate adsorbed on the resin were conducted in the same manner as described in Example 1 except for changing the temperature of pushing out and regeneration employed in Example 1 to room temperature. The amount of monomethyl adipate recovered in the effluent was 24 g, which was 78% in recovery percent.

The methanol remaining in the anion exchange resin column was pushed out in the same manner as described in Example 1.

Subsequently, 400 g of the oil layer from which methanol and potassium salt of monomethyl adipate had been removed was passed through the anion exchange resin column downwardly at room temperature at a flow rate of SV 1.0 again. Effluent amount flown out until the break through point of monomethyl adipate was 203 g and break through capacity was 0.99 meq/ml-resin. Purity of dimethyl sebacate in the effluent was 99.9% or more. Separation and purification of dimethyl sebacate from the effluent from the anion exchange resin column flown out until the break through point of monomethyl adipate was conducted by distillation.

Hydrolysis of dimethyl sebacate separated and purified from the electrolytic solution obtained by the electrolytic condensation was conducted in the same manner as described in Example 1.

EXAMPLE 6

Production of monomethyl adipate by half esterification of adipic acid was conducted in the same manner as described in Example 5 except for changing the ion exchange resin columns 2 and 3 in FIG. 1 to a reactor 2, and not to recycle a part of the reaction solution taken out of the drain 8 to the dissolving vessel 1. Conditions as to the reactor 2 were as follows: A starting material solution was fed from the dissolving vessel 1 to the reactor 2 at a rate of 60 kg/hr and the esterification reaction was carried out in the reactor 2 at a temperature of 180° C. with an average residence time of 5 hours. The composition of the starting material solution after 20 hours from the beginning of the reaction was 45.5% of adipic acid, 20.3% of dimethyl adipate, 10.8% of monomethyl adipate, 9.3% of methanol, 12.3% of water and 0.8% of cyclopentanone. From the reactor 2, the reaction solution was taken out at a rate of 60 kg/hr, the composition of said reaction solution being 21.7% of adipic acid, 20.0% of dimethyl adipate, 37.2% of monomethyl adipate, 4.3% of methanol, 15.6% of water and 0.9% of cyclopentanone. Changes of concentrations of cyclopentanone and iron ion in the reaction solution taken out of the reactor 2 with the lapse of time were as shown in Table 2 and curves A and B in FIG. 2.

TABLE 2

| Lapse of time (hours) | Concentration of cyclopentanone (%) | Concentration of iron ion (ppm) |
| --- | --- | --- |
| 20 | 0.9 | 15 |
| 50 | 1.2 | 20 |
| 100 | 2.0 | 40 |
| 150 | 3.2 | 70 |
| 200 | 4.6 | 105 |

As to materials of each apparatus, the reactor 2 was made of SUS 316 and materials for the dissolving vessel 1, distillation columns 4, 5 and 6 were the same as those of Example 5.

Using monomethyl adipate obtained by the half esterification of adipic acid, the electrolytic condensation was carried out in the same manner as described in Example 1.

In the next place, 100 ml (based on water standard) of an acrylic acid type weakly acidic cation exchange resin (Diaion WK-20, a trade name, manufactured by Mitsubishi Chemical Industries Ltd.) regenerated to the H type was substituted with methanol and packed in a jacketed column of inner diameter of 12 mm and 1500 mm long. Then, 500 g of the electrolytic solution obtained by the electrolytic condensation was passed through the cation exchange resin column downwardly at room temperature at a flow rate of SV 1.5. Effluent amount below 50 ppm of potassium ion concentration, which concentration is defined as the concentration of potassium ion at the break through point, was 360 g and break through capacity was 0.71 meq/ml-resin. In this case, break through capacity was calculated by using the equation described in Example 1 wherein monomethyl adipate was replaced with potassium ion. (In case of other cation exchange resin treatments, the same method as mentioned above will be used hereinafter.)

Subsequently, while passing warm water of 55° C. through the jacket of the cation exchange resin column, 200 g of monomethyl adipate and 150 g of methanol, each preheated at 55° C., were passed through the cation exchange resin column in this order upwardly at a flow rate of SV 1.5 to push out the remaining solution in the cation exchange resin column and to desorb the potassium ions adsorbed on the resin. The amount of potassium ions recovered in the effluent was 2.1 g, which was 45% in recovery percent. In this case, recovery percent was calculated by using the equation described in Example 1 wherein monomethyl adipate was replaced with potassium ion. (In case of other cation exchange resin treatments, the same method as mentioned above will be used hereinafter.)

After cooling the cation exchange resin column to room temperature, 500 g of the electrolytic solution was passed through the cation exchange resin column downwardly at room temperature at a flow rate of SV 1.5 again. Effluent amount flown out until the break through point of potassium ion was 290 g and break through capacity was 0.55 meq/ml-resin.

Then, methanol was removed by distillation from the electrolytic solution from which potassium ions had been removed so as to reduce the methanol concentration in the remaining solution to 2.5%. In the next place, 100 ml (based on water standard) of a tertiary amine type weakly basic anion exchange resin (Diaion WA-30, a trade name, manufactured by Mitsubishi Chemical Industries Ltd.) regenerated to the OH type was substituted with the electrolytic solution from which methanol, monomethyl adipate and its potassium salt had been removed and packed in a jacketed column of inner diameter of 12 mm and 1500 mm long. Then, 200 g of a mixture prepared by adding 100 g of the electrolytic solution from which methanol, monomethyl adipate and its potassium salt had been removed to 100 g of the electrolytic solution from which potassium ions and methanol had been removed was passed through the anion exchange resin column downwardly at room temperature at a flow rate of SV 1.0. Effluent amount flown out until the break through point of monomethyl adipate was 175 g and break through capacity was 0.71 meq/ml-resin. Purity of dimethyl sebacate in the effluent was 99.9% or more.

Pushing out the remaining solution in the anion exchange resin column and desorption of the monomethyl adipate adsorbed on the resin were conducted in the same manner as described in Example 1. The amount of monomethyl adipate recovered in the effluent was 16 g, which was 81% in recovery percent. Then, the methanol in the anion exchange resin column was pushed out in the same manner as descrbed in Example 1.

Subsequently, 200 g of the previously prepared mixture from the electrolytic solution from which potassium ions and methanol had been removed and the electrolytic solution from which methanol, monomethyl adipate and its potassium salt had been removed was passed through the anion exchange resin column downwardly at room temperature at a flow rate of SV 1.0 again. Effluent amount flown out until the break through point of monomethyl adipate was 177 g and break through capacity was 0.72 meq/ml-resin. Purity of dimethyl sebacate in the effluent was 99.9% or more.

Separation and purification of dimethyl sebacate from the effluent from the anion exchange resin column flown out until the break through point of monomethyl adipate was conducted by distillation. Analysis of potassium ion was conducted by the atomic absorption analysis.

Hydrolysis of dimethyl sebacate separated and purified from the electrolytic solution obtained by the electrolytic condensation was conducted in the same manner as described in Example 1.

EXAMPLE 7

The process of Example 1 was repeated except for changing the separation of dimethyl sebacate from the electrolytic solution obtained by the electrolytic condensation as follows:

As a regenerant for the cation exchange resin, there was used 200 g of a methanol solution containing 10% of monomethyl adipate and 150 g of methanol in place of 200 g of monomethyl adipate and 150 g of methanol used in Example 6. Except for the use of the regenerant mentioned above, the procedure of Example 6 was repeated.

The results of the cation exchange resin column procedures were as follows:

(1) During the adsorption procedure, effluent amount flown out until the break through point of potassium ion was 355 g and break through capacity was 0.70 meq/ml-resin.

(2) During the regeneration procedure, the amount of potassium ion recovered in the effluent was 2.0 g, which was 42% in recovery percent.

(3) During the readsorption procedure, effluent amount flown out until the break through point of potassium ion was 275 g, and break through capacity was 0.51 meq/ml-resin.

EXAMPLE 8

The process of Example 1 was repeated except for changing the separation of dimethyl sebacate from the electrolytic solution obtained by the electrolytic condensation as follows:

Methanol in the electrolytic solution was removed by distillation so as to reduce the methanol concentration in the remaining solution to 2.5%.

Then, 100 ml (based on water standard) of an iminodiacetic acid type weakly acidic cation exchange resin (Diaion CR-10, a trade name, manufactured by Mitsubishi Chemical Industries Ltd.) treated to the Cl, H type was substituted with the electrolytic solution from which methanol, monomethyl adipate and its potassium salt had been removed and packed in a jacketed column of inner diameter of 12 mm and 1500 mm long. Through the cation exchange resin column, 700 g of a mixture obtained by adding 410 g of the electrolytic solution from which methanol, monomethyl adipate and its potassium salt had been removed to 290 g of the electrolytic solution from which methanol had been removed was passed downwardly at room temperature at a flow rate of SV 1.5. Effluent amount flown out until the break through point of potassium ion was 442 g and break through capacity was 0.87 meq/ml-resin.

Then, while passing warm water of 55° C. through the jacket of the cation exchange resin column, 100 g of monomethyl adipate, 200 g of a methanol solution containing 10% of monomethyl adipate, and 150 g of methanol, each preheated at 55° C., were passed in this order through the cation exchanges resin column upwardly at a flow rate of SV 1.5 to conduct pushing out of the remaining solution in the cation exchange resin column and desorption of the potassium ions adsorbed on the resin. The amount of potassium ion recovered in the effluent was 2.7 g, which was 48% in recovery percent.

After cooling the cation exchange resin column to room temperature, 150 g of the electrolytic solution from which methanol, monomethyl adipate and its potassium salt had been removed was passed through the cation exchange resin column upwardly at room temperature at a flow rate of SV 1.5 to push out the remaining regenerant solution. Methanol concentration in the effluent was reduced to 4.5%.

Subsequently, 700 g of the mixture prepared from the electrolytic solution from which methanol had been removed and the electrolytic solution from which methanol, monomethyl adipate and its alkali metal salt had been removed as mentioned above was passed through the cation exchange resin column downwardly at room temperature at a flow rate of SV 1.5. Effluent amount flown out until the break through point of potassium ion was 330 g and break through capacity was 0.61 meq/ml-resin.

Then, a tertiary amine type weakly basic anion exchange resin (Amberlite IRA-94, a trade name, manufactured by Rohm & Haas Co.) regenerated to the OH type was packed in a column in the same manner as described in Example 1. Through the anion exchange resin column, 400 g of the effluent flown out until the break through point of potassium ion from the cation exchange resin column was passed in the same manner as described in Example 1. Effluent amount flown out until the break through point of monomethyl adipate was 225 g and break through capacity was 0.72 meq/ml-resin. Purity of dimethyl sebacate in the effluent was 99.9% or more.

Pushing out of the remaining solution in the anion exchange resin column and desorption of the monomethyl adipate adsorbed on the resin were conducted in the same manner as described in Example 1. The amount of monomethyl adipate recovered in the effluent was 18 g, which was 79% in recovery percent.

After pushing out the remaining regenerant solution in the anion exchange resin column in the same manner as described in Example 1, 300 g of the effluent flown out until the break through point of potassium ion from the cation exchange resin column was passed through the anion exchange resin column again. Effluent amount flown out until the break through point of monomethyl adipate was 220 g and break through capacity was 0.71 meq/ml-resin. Purity of dimethyl sebacate in the effluent was 99.9% or more.

Separation and purification of dimethyl sebacate from the effluent from the anion exchange resin column flown out until the break through point of monomethyl adipate was conducted by distillation.

EXAMPLE 9

The process of Example 1 was repeated except for changing the separation of dimethyl sebacate from the electrolytic solution obtained by the electrolytic condensation as follows:

The procedure of Example 8 was repeated except for changing the pretreatment of the iminodiacetic acid type weakly acidic anion exchange resin (Diaion CR-10) as follows.

The ion exchange resin treated to the OH, Na type as pretreatment was substituted with water and packed in a jacketed column of inner diameter of 12 mm and 1500 mm long. While passing warm water of 55° C. through the jacket, a 16% monomethyl adipate aqueous solution preheated at 55° C. was passed the column downwardly at a flow rate of SV 1.5 in an amount of 15 times as much as the amount of the resin (based on water standard) to desorb the sodium ion adsorbed on the resin. Subsequently, while passing warm water through the jacket of the column, methanol preheated at 55° C. was passed through the column downwardly at a flow rate of SV 1.5 in an amount of 15 times as much as the amount of the resin to desorb the monomethyl adipate adsorbed on the resin. Then, the methanol in the column was substituted with water.

The results of the cation exchange resin column procedures were as follows:

(1) During the adsorption procedure, effluent amount flown out until the break through point of potassium ion was 403 g and break through capacity was 0.78 meq/ml-resin.

(2) During the regeneration procedure, the amount of potassium ion recovered in the effluent was 3.2 g, which was 59% in recovery percent.

(3) During the readsorption procedure, effluent amount flown out until the break through point of potassium ion was 373 g, and break through capacity was 0.71 meq/ml-resin.

EXAMPLE 10

The process of Example 1 was repeated except for changing the separation of dimethyl sebacate from the electrolytic solution obtained by the electrolytic condensation as follows:

The procedure of Example 8 was repeated except for using a phosphonic acid type intermediately acidic cation exchange resin (Bio-Rex 63, a trade name, manufactured by Bio-Rad Co.) regenerated to the H type in place of the iminodiacetic acid type weakly acidic cation exchange resin treated to the Cl, H type.

The results of the cation exchange resin column procedures were as follows.

(1) During the adsorption procedure, effluent amount flown out until the break through point of potassium ion was 575 g and break through capacity was 1.18 meq/ml-resin.

(2) During the regeneration procedure, the amount of potassium ion recovered in the effluent was 4.4 g, which was 52% in recovery percent.

(3) During the readsorption procedure, effluent amount flown out until the break through point of potassium ion was 532 g and break through capacity was 1.08 meq/ml-resin.

EXAMPLE 11

The process of Example 1 was repeated except for changing the separation of dimethyl sebacate from the electrolytic solution obtained by the electrolytic condensation as follows:

As an amphoteric ion exchange resin, a resin produced by suspension polymerizing acrylic acid, chloromethylated styrene and divinylbenzene and treating the resulting copolymer with diethylamine was used. Exchange capacity of the amino group was 0.87 meq/ml-resin and exchange capacity of the carboxyl group was 0.84 meq/ml-resin.

Methanol was removed by distillation from the above-mentioned electrolytic solution to reduce the concentration to 2.5%. To 300 g of the electrolytic solution from which methanol had thus been removed, 600 g of the electrolytic solution from which methanol, monomethyl adipate and its potassium salt had been removed was added to prepare 900 g of a feeding solution to the ion exchange resin column.

Then, 150 ml (based on water standard) of the amphoteric ion exchange resin treated to the OH, Na type was substituted with water and packed in a jacketed column of inner diameter of 12 mm and 1500 mm long. While passing warm water of 55° C. through the jacket of the ion exchange resin column, 1500 g of a 16% monomethyl adipate aqueous solution preheated at 55° C. was passed through the ion exchange resin column upwardly at a flow rate of SV 1.5 to desorb the sodium ion adsorbed on the resin. Subsequently, while passing warm water of 55° C. through the jacket of the ion exchange resin column, 1500 ml of methanol preheated at 55° C. was passed through the ion exchange resin column upwardly at a flow rate of SV 1.5 to desorb the monomethyl adipate adsorbed on the resin.

After cooling the ion exchange resin column to room temperature, 225 g of the electrolytic solution from which methanol, monomethyl adipate and its potassium salt had been removed was passed through the ion exchange resin column upwardly at room temperature at a flow rate of SV 1.5 to push out the methanol. Methanol concentration in the effluent was reduced to 4.5%.

Through the ion exchange resin column packed with the amphoteric ion exchange resin treated by the method as mentioned above, 900 g of the feeding solution previously prepared was passed downwardly at room temperature at a flow rate of SV 1.0. Effluent amount of the solution in which potassium ion concentration was 50 ppm or less and monomethyl adipate concentration was 0.05% or less was 249 g. Effluent amount of the solution in which monomethyl adipate concentration was more than 0.05% and potassium ion concentration was 50 ppm or less was 329 g. Break through capacity of monomethyl adipate was 0.41 meq/ml-resin. Purity of dimethyl sebacate in the solution flown out until the break through point of monomethyl adipate was 99.9% or more. Break through capacity of potassium ion was 0.30 meq/ml-resin. Break through capacity was calculated according to the following equation:

$$\text{Break through capacity} = \frac{(W_F - W_G) C_D}{V_B M_B (100 - C_E)} \times 1000$$

wherein $W_F$ is the effluent amount flown out until the break through point (grams), $W_G$ is the amount of the solution which substitutes the resin (grams), $C_D$ is the concentration of monomethyl adipate (including potassium salt of monomethyl adipate) or the concentration of potassium ion in the feeding solution to the ion exchange resin column (percents), $C_E$ is the difference between the total concentrations of monomethyl adipate and its potassium salt in the feeding solution to the ion exchange resin column and the total concentrations of monomethyl adipate and its potassium salt in the effluent flown out until the break through point (percents), $V_B$ is the volume of the resin (based on water standard) (ml), and $M_B$ *is the molecular weight of monomethyl adipate or potassium.*

Then, while passing warm water of 55° C. through the jacket of the ion exchange resin column, 375 ml of methanol preheated at 55° C. was passed through the ion exchange resin column upwardly at a flow rate of SV 1.5 to push out the remaining solution in the ion exchange resin column and to desorb the monomethyl adipate and potassium ions adsorbed on the resin. The amount of monomethyl adipate (including that of potassium salt of monomethyl adipate) recovered in the effluent was 20 g, which was 72% in recovery percent. The amount of potassium ion recovered in the effluent was 2.7 g, which was 51% in recovery percent. Recovery percent was calculated according to the following equation:

$$\text{Recovery percent} = \frac{W_H - W_I}{W_J} \times 100$$

wherein $W_H$ is the amount of monomethyl adipate (including potassium salt of monomethyl adipate) or potassium ion recovered in the effluent (grams), $W_I$ is the amount of monomethyl adipate (including potassium salt of monomethyl adipate) or potassium ion in the remaining solution in the ion exchange resin column (grams), and $W_J$ is the amount of the monomethyl adipate or potassium ion adsorbed on the resin (grams).

After cooling the ion exchange resin column to room temperature, 225 g of the electrolytic solution from which methanol, monomethyl adipate and its potassium salt had been removed was passed through the ion exchange resin column upwardly at room temperature at a flow rate of SV 1.5 to push out the methanol. Methanol concentration in the effluent was reduced to 4.5%.

Subsequently, 900 g of the feeding solution to the ion exchange resin column previously prepared from the electrolytic solution from which methanol had been removed and the electrolytic solution from which methanol, monomethyl adipate and its potassium salt had been removed was passed through the ion exchange resin column downwardly again at room temperature at a flow rate of SV 1.0. Effluent amount flown out until the break through point of monomethyl adipate was 245 g and break through capacity was 0.40 meq/ml-resin. Effluent amount flown out until the break through point of potassium ion was 322 g and break through capacity was 0.29 meq/ml-resin. Purity of dimethyl sebacate in the effluent flown out until the break through point of monomethyl adipate was 99.9% or more.

Separation and purification of dimethyl sebacate from the effluent from the ion exchange resin column flown out until the break through point of monomethyl adipate was conducted by distillation.

EXAMPLE 12

The process of Example 1 was repeated except for changing the separation of dimethyl sebacate from the electrolytic solution obtained by the electrolytic condensation as follows:

Methanol was removed by distillation from the electrolytic solution so as to reduce the methanol concentration in the remaining solution to 2.5%. To 300 g of the electrolytic solution from which methanol had thus been removed, 600 g of the electrolytic solution from which methanol, monomethyl adipate and its potassium salt had been removed was added to prepare 900 g of a feeding solution to the ion exchange resin column.

Subsequently, 50 ml (based on water standard) of a phosphonic acid type intermediately acidic cation exchange resin (Bio-Rex 63, a trade name, manufactured by Bio-Rad Co.) regenerated to the H type and 150 ml (based on water standard) of a tertiary amine type weakly basic anion exchange resin (Dowex HWA-1, a trade name, manufactured by Dow Chemical Co.) regenerated to the OH type were mixed sufficiently and substituted with the electrolytic solution from which methanol, monomethyl adipate and its potassium salt had been removed, and packed in a jacketed column of inner diameter of 12 mm and 2000 mm long. Then, 900 g of the feeding solution previously prepared was passed through the mixed-bed system ion exchange resin column downwardly at room temperature at a flow rate of SV 1.0. The amount of the effluent in which monomethyl adipate concentration was 0.05% or less and potassium ion concentration was 50 ppm or less was 254 g. The amount of the effluent in which monomethyl adipate concentration was more than 0.05% and potassium ion concentration was 50 ppm or less was 9 g. Break through capacity of monomethyl adipate was 0.50 meq/ml-resin and break through capacity of potassium ion was 0.26 meq/ml-resin. Purity of dimethyl sebacate in the effluent flown out until the break through point of monomethyl adipate was 99.9% or more. The break through capacity was calculated in the same manner as described in Example 11.

While passing warm water of 55° C. through the jacket of the ion exchange resin column, 200 g of monomethyl adipate and 300 ml of methanol, each preheated at 55° C., was passed in this order through the ion exchange resin column upwardly at a flow rate of SV 1.5 to push out the remaining solution in the ion exchange resin column and to desorb the monomethyl adipate and potassium ion adsorbed on the resin. Potassium ion recovered in the effluent was 3 g, which was 56% in recovery percent. The recovery percent was calculated in the same manner as described in Example 11, but recovery percent of monomethyl adipate was not obtained.

After cooling the ion exchange resin column to room temperature, 300 g of the electrolytic solution from which methanol, monomethyl adipate and its potassium salt had been removed was passed through the ion exchange resin column upwardly at room temperature at a flow rate of SV 1.5 to push out the methanol. Methanol concentration in the effluent was reduced to 4.5%.

Then, 900 g of the feeding solution previously prepared from the electrolytic solution from which methanol had been removed and the electrolytic solution from which methanol, monomethyl adipate and its potassium salt and been removed was passed through the ion exchange resin column downwardly at room temperature at a flow rate of SV 1.0 again. Effluent amount flown out until the break through point of monomethyl adipate was 252 g and break through capacity was 0.49 meq/ml-resin. Effluent amount flown out until the break through point of potassium ion was 261 g and break through capacity was 0.25 meq/ml-resin. Purity of dimethyl sebacate in the effluent flown out until the break through point of monomethyl adipate was 99.9% or more.

Separation and purification of dimethyl sebacate from the effluent from the ion exchange resin column flown out until the break through point of monomethyl adipate was conducted by distillation.

EXAMPLE 13

The process of Example 2 was repeated except for changing water concentration in the electrolytic solution as shown in Table 3 in the electrolytic condensation of monomethyl adipate obtained by the half esterification of adipic acid. The results were as shown in Table 3.

TABLE 3

| Run No. | Water concentration (%) | Current efficiency (%) | Material yield (%) | Voltage (V) |
|---|---|---|---|---|
| 1 | 0.12 | 0.4 | — | 5.9 |
| 2 | 0.15 | 67.3 | 80.6 | 7.5 |
| 3 | 0.85 | 67.9 | 80.7 | 7.8 |
| 4 | 1.51 | 66.5 | 79.3 | 7.8 |
| 5 | 3.05 | 66.4 | 81.4 | 7.5 |
| 6 | 3.56 | 56.3 | 71.1 | 7.6 |

EXAMPLE 14

The process of Example 1 was repeated except for carrying out hydrolysis of dimethyl sebacate separated and purified from the electrolytic solution obtained by the electrolytic condensation as follows:

A mixture containing dimethyl sebacate, sebacic acid and water as shown in Table 4 was placed in a 1 liter autoclave and the reaction was carried out at 180° C. with vigorous stirring. An initially ununiform reaction solution became a uniform solution in the course of the reaction. From the time when the reaction solution became a uniform solution, methanol and water were continuously removed by distillation from the autoclave while at the same time insufficient water caused by the removal of water together with methanol was supplemented continuously to the autoclave to carry out the reaction for an additional 5 hours. During the reaction, inner pressure of the autoclave was 7 to 9 kg/cm$^2$ (gauge). Time required for forming a uniform solution, a total amount of methanol and water removed by distillation until the end of the reaction, a total amount of water fed and conversion by hydrolysis were as shown in Table 4.

TABLE 4

| Run No. | Charging amount (g) | | | Time required for forming a uniform solution (hrs) | Total amount of methanol and water distilled off (g) | Total amount of water fed (g) | Conversion by hydrolysis (mole %) |
|---|---|---|---|---|---|---|---|
| | Dimethyl sebacate | Sebacic acid | Water | | | | |
| 1 | 200 | 0 | 200 | 6.4 | 630 | 655 | 99.1 |
| 2 | 190 | 9 | 200 | 3.0 | 640 | 660 | 99.3 |
| 3 | 180 | 18 | 200 | 2.4 | 595 | 610 | 99.5 |
| 4 | 140 | 53 | 200 | 1.0 | 510 | 535 | 99.4 |

EXAMPLE 15

The process of Example 1 was repeated except for carrying out hydrolysis of dimethyl sebacate separated and purified from the electrolytic solution obtained by the electrolytic condensation as follows:

To a 1 liter autoclave, 400 g of a solution containing 48% of dimethyl sebacate, 2% of sebacic acid and 50% of water was placed and the first half of the reaction was carried out with vigorous stirring at a temperature as shown in Table 5 until the reaction solution became a uniform solution. From the time when the reaction solution become a uniform solution, the reaction temperature was set at 160° C. and the reaction was continued for an additional 5 hours while removing methanol and water continuously by distillation from the autoclave and at the same time continuously supplementing insufficient water caused by the removal of water together with methanol. A total amount of methanol and water distilled off until the end of the reaction was 650 g and a total amount of water fed was 680 g. During the latter half of the reaction, inner pressure of the autoclave was 5 to 6 kg/cm$^2$ (gauge). Reaction temperature in the first half of the reaction, time required for forming a uniform solution, and conversion by hydrolysis were as shown in Table 5.

TABLE 5

| Run No. | Reaction temp. in the first half of the reaction (°C.) | Time required for forming a uniform solution (hrs) | Conversion by hydrolysis (mole %) |
|---|---|---|---|
| 1 | 160 | 12.5 | 99.2 |
| 2 | 120 | 3.1 | 99.4 |
| 3 | 200 | 1.9 | 99.3 |

What is claimed is:

1. A process for producing sebacic acid from adipic acid which comprises:
   half esterifying adipic acid with methanol to produce monomethyl adipate,
   conducting electrolytic condensation of the monomethyl adipate in a methanol solution containing an alkali metal salt of monomethyl adipate to give an electrolytic solution containing dimethyl sebacate,
   recovering dimethyl sebacate from the electrolytic solution by extracting the alkali metal salt of monomethyl adipate from the electrolytic solution with water after removal of the methanol by distillation and treating the electrolytic solution with an anion exchanger packed in a fixed bed to separate the monomethyl adipate therefrom, the water extraction and the anion exchange treatment being carried out successively or simultaneously,
   and hydrolyzing the resulting dimethyl sebacate to produce sebacic acid.

2. A process according to claim 1, wherein the half esterification of adipic acid is carried out in the presence of a strongly acidic cation exchange resin.

3. A process according to claim 2, wherein the half esterification of adipic acid is carried out by using a starting material solution containing 0.2 to 2 moles dimethyl adipate, 0.5 to 5 moles of methanol and 1 to 10 moles of water per mole of adipic acid and passing the starting material solution through a fixed bed packed with the strongly acidic cation exchange resin.

4. A process according to claim 3, wherein the half esterification of adipic acid is carried out at a temperature of 60° to 90° C. and a part of an effluent from the fixed bed is returned to the starting material solution.

5. A process according to claim 1, wherein the electrolytic condensation of monomethyl adipate is carried out in the electrolytic solution having a water concentration of 0.15 to 3.0% by weight.

6. A process according to claim 5, wherein the electrolytic condensation of monomethyl adipate is carried out by using the electrolytic solution containing 5 to 20% by weight of monomethyl adipate, neutralization degree of monomethyl adipate being 20 to 50% by mole and the base for neutralizing monomethyl adipate being a hydroxide, a methylate, a carbonate, or a bicarbonate of sodium or potassium, and 10 to 30% by weight of dimethyl sebacate, under the conditions of a flow rate of the electrolytic solution in an electrolytic cell of 1 to 3 m/sec, an electrode distance of 0.5 to 2 mm, current density of 10 to 30 A/dm$^2$ and an electrolytic solution temperature of 50° to 60° C.

7. A process according to claim 1, wherein the water extraction is carried out by using 5 to 50% by weight of water based on the weight of the electrolytic solution after removing methanol.

8. A process according to claim 1, wherein the anion exchanger is a weakly basic, intermediately basic or pyridinium type anion exchange resin.

9. A process according to claim 8, wherein the weakly or intermediately basic anion exchange resin is a tertiary amine type anion exchange resin.

10. A process according to claim 1, wherein the anion exchanger is a weakly basic, intermediately basic or pyridinium type anion exchange resin and the methanol concentration in the feeding solution to the fixed bed packed with the anion exchanger is 5% by weight or less.

11. A process according to claim 1, wherein regeneration of the anion exchanger is carried out by using methanol or warm water.

12. A process according to claim 11, wherein the methanol is that removed from the electrolytic solution.

13. A process according to claim 11, wherein the anion exchanger is a weakly or intermediately basic anion exchange resin and the warm water is that of 80° to 90° C.

14. A process according to claim 1, wherein the removal of methanol from the electrolytic solution is carried out before the anion exchange treatment, regeneration of the anion exchanger is carried out by using methanol, and remaining methanol in the anion exchanger is substituted with water or an electrolytic solution from which methanol, monomethyl adipate and its alkali metal salt have been removed.

15. A process according to claim 1, wherein the hydrolysis of dimethyl sebacate is carried out by adding sebacic acid, and removing methanol produced by the hydrolysis out of the system during the hydrolysis.

16. A process according to claim 15, wherein the amount of sebacic acid to be added is 1 to 20% by weight based on the weight of dimethyl sebacate charged and a water concentration in the reaction solution is maintained at 10 to 75% by weight during the hydrolysis and the hydrolysis is carried out in the first half of the reaction in which the reaction solution is an ununiform solution at a temperature of 180° to 220° C. and in the latter half of the reaction in which the reaction solution is a uniform solution at a temperature of 150° to 220° C.

17. A process according to claim 15, wherein the removal of methanol is conducted in the latter half of the reaction in which the reaction solution is a uniform solution and a total removing amount of methanol together with water is 2 to 6 parts by weight based on 1 part by weight of dimethyl sebacate charged.

18. A process for producing sebacic acid from adipic acid which comprises
half esterifying adipic acid with methanol to produce monomethyl adipate,
conducting electrolytic condensation of the monomethyl adipate in a methanol solution containing an alkali metal salt of monomethyl adipate to give an electrolytic solution containing dimethyl sebacate,
recovering dimethyl sebacate from the electrolytic solution by treating the electrolytic solution with a cation exchanger packed in a fixed bed to separate the alkali metal ions therefrom, treating the electrolytic solution with an anion exchanger packed in a fixed bed to separate the monomethyl adipate therefrom, the cation exchange treatment and the anion exchange treatment being carried out successively in this order or simultaneously, and removing the methanol from the electrolytic solution by distillation prior to the anion exchange treatment, and hydrolyzing the resulting dimethyl sebacate to produce sebacic acid.

19. A process according to claim 18, wherein the half esterification of adipic acid is carried out in the presence of a strongly acidic cation exchange resin.

20. A process according to claim 18, wherein the electrolytic condensation of monomethyl adipate is carried out in the electrolytic solution having a water concentration of 0.15 to 3.0% by weight.

21. A process according to claim 18, wherein the cation exchange treatment and the anion exchange treatment are carried out in this order successively using as the cation exchanger a weakly or intermediately acidic cation exchange resin and the anion exchanger a weakly basic or intermediately basic or pyridinium type anion exchange resin.

22. A process according to claim 21, wherein the weakly acidic cation exchange resin is an acrylic acid type or iminodiacetic acid type cation exchange resin.

23. A process according to claim 21, wherein the intermediately acidic cation exchange resin is a phosphonic acid type cation exchange resin.

24. A process according to claim 21, wherein the weakly or intermediately basic anion exchange resin is a tertiary amine type anion exchange resin.

25. A process according to claim 21, wherein the methanol concentration in the feeding solution to the fixed bed packed with the anion exchanger is 5% by weight or less.

26. A process according to claim 21, wherein regeneration of the cation exchanger is conducted by using monomethyl adipate and/or a methanol solution containing monomethyl adipate and regeneration of the anion exchanger is conducted by using methanol.

27. A process according to claim 26, wherein the monomethyl adipate is obtained from the half esterification of adipic acid.

28. The process according to claim 26, wherein the methanol solution containing monomethyl adipate for the regeneration of the cation exchanger is an effluent from the regeneration of the anion exchanger.

29. A process according to claim 26, wherein the methanol for the regeneration of the anion exchanger is that removed from the electrolytic solution.

30. A process according to claim 26, wherein the removal of methanol is conducted before the ion exchange treatments and remaining regenerant solution in the ion exchangers is substituted with an electrolytic solution from which methanol, monomethyl adipate and its alkali metal salt have been removed.

31. A process according to claim 18, wherein the cation exchange treatment and the anion exchange treatment are conducted at the same time by using an amphoteric ion exchange resin having both weakly or intermediately basic functional groups and weakly acidic functional groups in place of the cation exchanger and the anion exchanger.

32. A process according to claim 31, wherein the weakly or intermediately basic functional groups are tertiary amines and the weakly acidic functional groups are acrylic acid type functional groups.

33. A process according to claim 31, wherein regeneration of the amphoteric ion exchange resin is conducted by using methanol.

34. A process according to claim 18, wherein the cation exchange treatment and the anion exchange treatment are conducted at the same time by using a mixed-bed system of a weakly or intermediately acidic cation exchange resin and a weakly basic or intermediately basic or pyridinium type anion exchange resin.

35. A process according to claim 34, wherein regeneration of the cation exchange resin and the anion exchange resin in the mixed-bed system is conducted by using methanol or monomethyl adipate and methanol in this order.

36. A process according to claim 18, wherein the hydrolysis of dimethyl sebacate is carried out by adding sebacic acid, and removing methanol produced by the hydrolysis out of the system during the hydrolysis.

* * * * *